(12) United States Patent
Suzuki et al.

(10) Patent No.: US 6,994,922 B2
(45) Date of Patent: Feb. 7, 2006

(54) ORGANIC LUMINESCENCE DEVICE WITH A FUSED POLYNUCLEAR COMPOUND

(75) Inventors: Koichi Suzuki, Kanagawa (JP); Akihiro Senoo, Kanagawa (JP); Hiroshi Tanabe, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 16 days.

(21) Appl. No.: 10/940,734

(22) Filed: Sep. 15, 2004

(65) Prior Publication Data

US 2005/0048318 A1    Mar. 3, 2005

Related U.S. Application Data

(62) Division of application No. 10/077,800, filed on Feb. 20, 2002, now Pat. No. 6,830,829.

(30) Foreign Application Priority Data

Feb. 22, 2001 (JP) ............................. 2001-046225
Feb. 14, 2002 (JP) ............................. 2002-036804

(51) Int. Cl.
 *H05B 33/14* (2006.01)
(52) U.S. Cl. ...................... 428/690; 428/917; 313/504; 313/506
(58) Field of Classification Search ................ 428/690, 428/917; 313/504, 506; 252/301.16
 See application file for complete search history.

(56) References Cited

U.S. PATENT DOCUMENTS

| | | | |
|---|---|---|---|
| 4,539,507 A | 9/1985 | VanSlyke et al. | 313/504 |
| 4,720,432 A | 1/1988 | VanSlyke et al. | 428/457 |
| 4,885,211 A | 12/1989 | Tang et al. | 428/457 |
| 5,077,142 A | 12/1991 | Sakon et al. | 428/690 |
| 5,130,603 A | 7/1992 | Tokailin et al. | 313/504 |
| 5,151,629 A | 9/1992 | VanSlyke | 313/504 |
| 5,227,252 A | 7/1993 | Murayama et al. | 428/690 |
| 5,247,190 A | 9/1993 | Friend et al. | 257/40 |
| 5,317,169 A | 5/1994 | Nakano et al. | 257/40 |
| 5,382,477 A | 1/1995 | Saito et al. | 428/690 |
| 5,409,783 A | 4/1995 | Tang et al. | 428/690 |
| 5,514,878 A | 5/1996 | Holmes et al. | 257/40 |
| 5,536,949 A | 7/1996 | Hosokawa et al. | 257/40 |
| 5,635,308 A | 6/1997 | Inoue et al. | 428/690 |
| 5,645,948 A | 7/1997 | Shi et al. | 428/690 |
| 5,672,678 A | 9/1997 | Holmes et al. | 528/373 |
| 5,726,457 A | 3/1998 | Nakano et al. | 257/40 |
| 5,766,779 A | 6/1998 | Shi et al. | 428/690 |
| 6,093,864 A | 7/2000 | Tokailin et al. | 585/25 |
| 6,203,933 B1 | 3/2001 | Nakaya et al. | 428/690 |
| 6,596,415 B2 | 7/2003 | Shi et al. | 428/690 |
| 6,635,364 B1 | 10/2003 | Igarashi | 428/690 |
| 6,830,829 B2 * | 12/2004 | Suzuki et al. | 428/690 |

FOREIGN PATENT DOCUMENTS

| JP | 2-247278 | 10/1990 |
|---|---|---|
| JP | 3-255190 | 11/1991 |
| JP | 4-68076 | 3/1992 |
| JP | 4-145192 | 5/1992 |
| JP | 5-32966 | 2/1993 |
| JP | 5-202356 | 8/1993 |
| JP | 5-247460 | 9/1993 |
| JP | 6-228552 | 8/1994 |
| JP | 6-240244 | 8/1994 |
| JP | 7-109454 | 4/1995 |
| JP | 8-311442 | 11/1996 |
| JP | 9-202878 | 8/1997 |
| JP | 9-227576 | 9/1997 |
| JP | 9-241629 | 9/1997 |
| JP | 2000-26334 | 1/2000 |
| JP | 2000-268964 | 9/2000 |
| JP | 2001-192651 | 7/2001 |

OTHER PUBLICATIONS

Norio Miyaura et al., "Palladium-Catalyzed Cross-Coupling Reactions of Organoboron Compounds," 95(7) *Chem. Rev.* 2457-2483 (1995).

Takakazu Yamamoto et al., "A Novel Type of Polycondensation Utilizing Transition Metal-Catalyzed C-C Coupling—I. Preparation of Thermostable Polyphenylene Type Polymers," 51(7) *Bull. Chem. Soc. Jpn.* 2091-2097 (1978).

(Continued)

*Primary Examiner*—Marie Yamnitzky
(74) *Attorney, Agent, or Firm*—Fitzpatrick, Cella, Harper & Scinto

(57) ABSTRACT

An organic luminescence device having an anode and a cathode and at least one organic luminescence function layer disposed between the anode and the cathode. At least one organic luminescence function layer described above includes a layer of a fused polynuclear compound represented by the following formula (I):

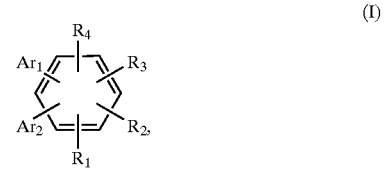

wherein $R_1$, $R_2$, $R_3$ and $R_4$ independently denote hydrogen atom, an alkyl group, a substituted or unsubstituted aralkyl group, a substituted or unsubstituted aryl group, a substituted or unsubstituted heterocyclic group, a substituted amino group or cyano group; and $Ar_1$ and $Ar_2$ independently denote a substituted or unsubstituted fused polynuclear aromatic group or a substituted or unsubstituted fused polynuclear heterocyclic group.

2 Claims, 3 Drawing Sheets

OTHER PUBLICATIONS

F.J. Weigert, "HZSM-5-Catalyzed Isomerization of Alkylanilines," 52(15) *J. Org. Chem.* 3296-3298 (1987).

C.W. Tang et al., "Organic Luminescent Diodes," 51(12) *Appl. Phys. Lett.* 913-915 (Sep. 1987).

J.H. Burroughes et al., "Light-Emitting Diodes Based on Conjugated Polymers," 347 *Nature* 539-541 (Oct. 1990).

Yasuhiko Shirota et al., "Development of Hole-Blocking Amorphous Molecular Materials and Their Application in Organic Light-Emitting Diodes," in *Organic Light-Emitting Materials, Proceedings of SPIE*, vol. 4464, pp. 203-210 (2002).

* cited by examiner

ORGANIC LUMINESCENCE DEVICE WITH A FUSED POLYNUCLEAR COMPOUND

This application is a division of application Ser. No. 10/077,800, filed Feb. 20, 2002, now U.S. Pat. No. 6,830,829, which is incorporated herein by reference.

FIELD OF THE INVENTION AND RELATED ART

The present invention relates to a specific fused polynuclear (or polycyclic) compound and an organic luminescence device using the fused polynuclear compound. An organic luminescence device is a device such that a thin film containing a fluorescent organic compound is sandwiched between an anode and a cathode, and holes nd electrons are injected from the anode and the cathode, respectively, into the fluorescent organic compound layer to generate excitons, which emit light at the time of being returned to a ground state.

More specifically, according to Kodak's study (Appl. Phys. Lett., 51,913 (1987)), when a voltage of ca. 10 volts is applied to a function separation-type organic luminescence device including two layers of an aluminum quinolinol complex (as electron transport and luminescence material) and a triphenylamine derivative (as hole transport material) disposed between an anode of ITO (indium tin oxide) and a cathode of a magnesium-silver alloy, an emission luminance of ca. 1000 $cd/m^2$ is obtained. Related patents thereof are, e.g., U.S. Pat. Nos. 4,539,507; 4,720,432; and 4,885,211.

Further, it is impossible to effect luminescence ranging from ultraviolet region to infrared region by appropriately changing the species of a fluorescent organic compound used. In recent years, studies on various fluorescent organic compounds have been made extensively as, e.g., described in U.S. Pat. Nos. 5,151,629 5,409,783; and 5,382,477; and Japanese Laid-Open Patent Application (JP-A) Nos. 2-247278 (corr. to U.S. Pat. Nos. 5,130,603 and 6,093,864); 3-255190 (corr. to U.S. Pat. No. 5,227,252); 5-202356: 9-202878; and 9-227576.

In addition to the above-mentioned organic luminescence devices using low-molecular weight materials, an organic luminescence device using a conjugated system polymer has been reported by a research group of Kenbridge University ("Nature", 347,539 (1990)). According to this report, by forming a single layer of PPV (polyphenylenevinylene) by means of wet coating, luminescence from the layer has been confirmed.

Related patents as to organic luminescence devices using conjugated system polymers may include: U.S. Pat. Nos. 5,247,190; 5,514,878; and 5,672,678; JP-A 4-145192 (corr. to U.S. Pat. Nos. 5,317,169 and 5,726,457) and JP-A 5-247460.

As described above, recent progress of the organic luminescence devices is noticeable. More specifically, it is possible to realize a thin and light-weight luminescence device allowing high luminance at low applied voltage, variety of emission wavelength and high-speed responsiveness, thus suggesting possibilities of application to various uses.

However, the organic luminescence devices are required to exhibit further improved performances such as light output at high luminance and high conversion efficiency. Further, the organic luminescence devices have been accompanied with problems in terms of durability such as a change in luminance with time due to continuous use for a long time, and a deterioration (e.g., an occurrence of dark spots due to leakage of current) by ambient gas containing oxygen or by humidity. Moreover, in the case where the organic luminescence devices are applied to full-color displays, it is necessary to realize luminance of red (R), green (G) and blue (B) with good color purities but resultant color purities have been insufficient as yet.

As fluorescent organic compounds for use in an electron transport layer and/or a luminescence layer, a large number of aromatic compounds or fused polynuclear aromatic compounds have been proposed as described in, e.g., JP-A 4-68076, 5-32966, 6-228552, 6-240244, 7-109454, 8-311442 (corr. to U.S. Pat. No. 6,203,933), 9-241629, 2000-26334, and 2000-268964. However, resultant emission luminances and durabilities have been still insufficient.

SUMMARY OF THE INVENTION

A principal object of the present invention is to provide an organic luminescence device having solved the above-mentioned problems.

A specific object of the present invention is to provide an organic luminescence device capable of effecting output of light with very high efficiency and luminance by using a specific fused polynuclear aromatic compound.

Another object of the present invention is to provide an organic luminescence device having a high durability.

A further object of the present invention is to provide an organic luminescence device which can be prepared readily and relatively inexpensively.

According to the present invention, there is provided an organic luminescence device, comprising:

a pair of an anode and a cathode, and at least one organic luminescence function layer disposed between the anode and the cathode, wherein at least one organic luminescence function layer described above comprises a layer comprising at least one species of a fused polynuclear compound characterized by a substituted benzene structure having at least two fused polynuclear aromatic or heterocyclic groups as substituents.

The fused polynuclear compound used in the present invention is represented by any one of the following formulas (I) to (VII):

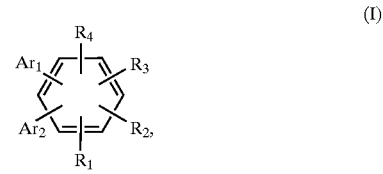
(I)

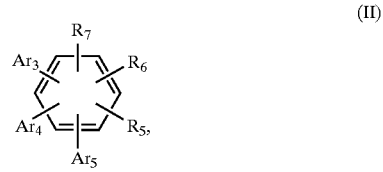
(II)

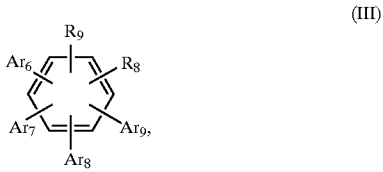
(III)

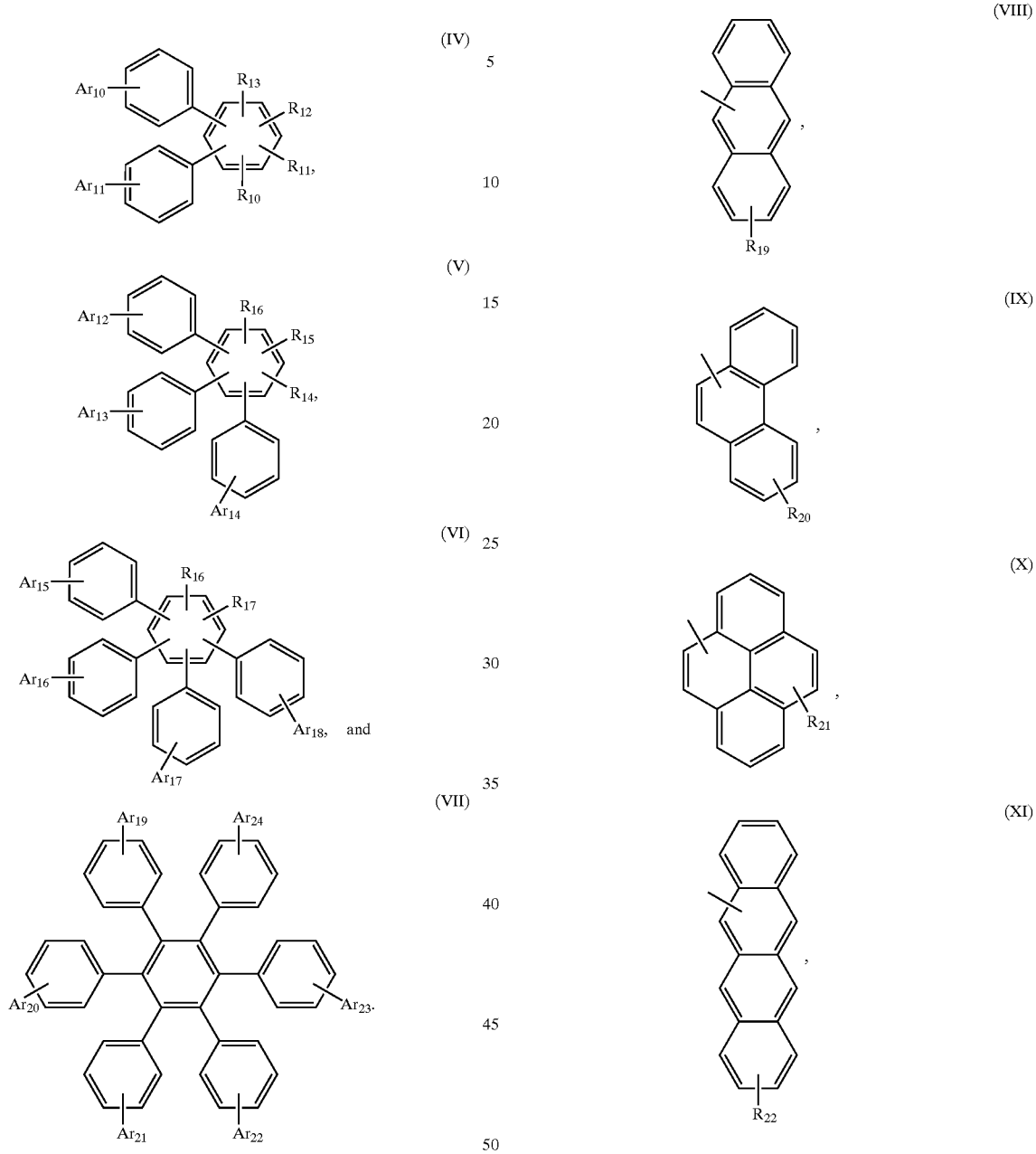

In the above formulas (I) to (VII), $R_1$ to $R_{18}$ independently denote hydrogen atom, an alkyl group, a substituted or unsubstituted aralkyl group, a substituted or unsubstituted aryl group, a substituted or unsubstituted heterocyclic group, a substituted amino group or cyano group; and $Ar_1$ to $Ar_{24}$ independently denote a substituted or unsubstituted fused polynuclear aromatic group br a substituted or unsubstituted fused polynuclear heterocyclic group.

In the present invention, $Ar_1$ to $Ar_{24}$ in the above-mentioned formulas (I) to (VII) may preferably denote a substituted or unsubstituted fused polynuclear group comprising at least three fused benzene rings or at least four fused benzene rings, more preferably be a fused polynuclear group represented by any one of the following formulas (VIII) to (XIII).

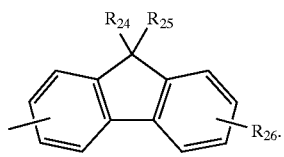

(XIII)

In the above formulas (VIII) to (XIII), $R_1$ to $R_{26}$ independently denote hydrogen atom, an aralkyl group, a substituted or unsubstituted aralkyl group, a substituted or unsubstituted aryl group, a substituted or unsubstituted heterocyclic group, a substituted amino group or cyano group.

In the present invention, when the above-mentioned at least one organic luminescence function layer comprises an electron transport layer and or a is luminescence layer, the electron transport layer or luminescence layer may preferably comprise a fused polynuclear compound represented by any one of the formulas (I) to (VII). In this case, in a more preferred embodiment, the luminescence layer comprises a fused polynuclear compound represented by any one of the formulas (I) to (VII) and a compound represented by the following formula:

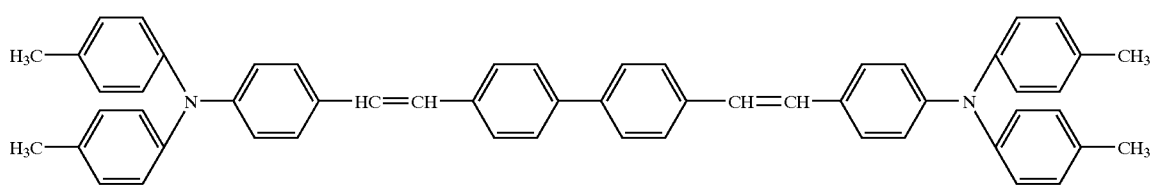

Further, when the above-mentioned at least one organic luminescence function layer comprises an electron transport layer and or a luminescence layer, the electron transport layer may preferably comprise a hole transporting material and a yellow luminescent material, and said luminescence later may preferably comprise a fused polynuclear compound represented by any one of the formulas (I) to (VII) and a compound represented by the following formula:

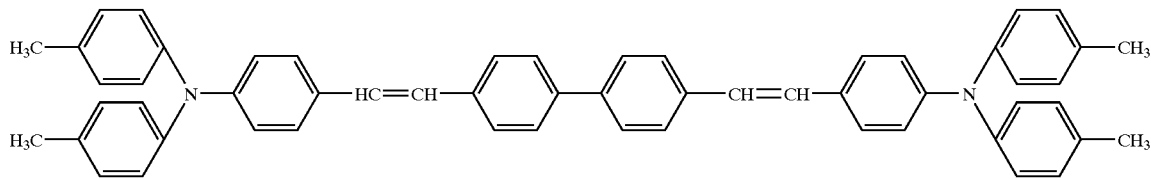

The fused polynuclear compound used in the present invention may preferably be represented by any one of the following formulas:

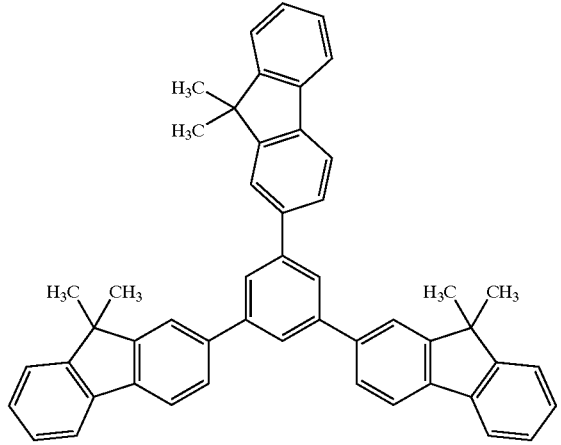

-continued
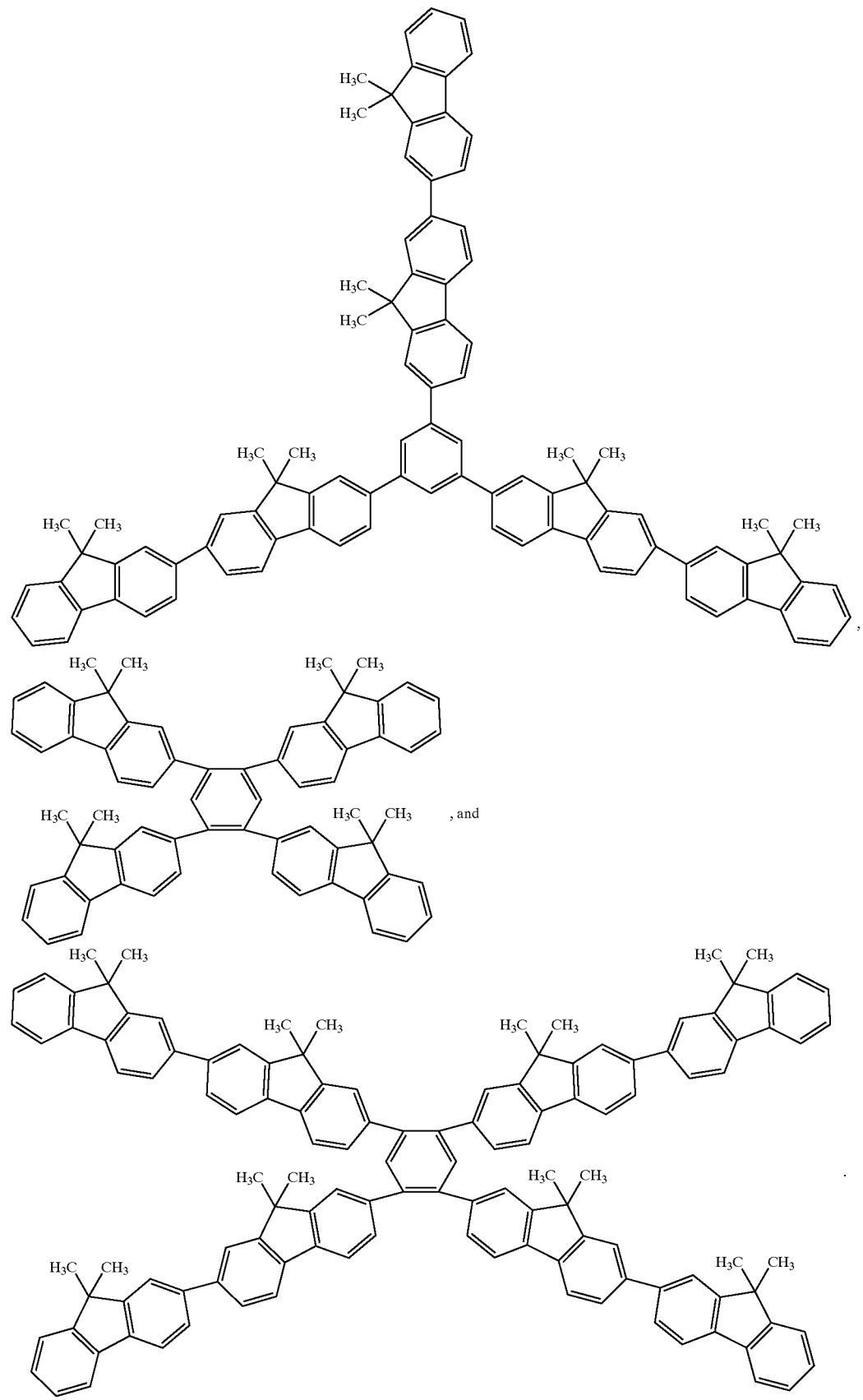

These and other objects, features and advantages of the present invention will become more apparent upon a consideration of the following description of the preferred embodiments of the present invention taken in conjunction with the accompanying drawings.

DESCRIPTION OF THE PREFERRED EMBODIMENTS

Figure 1:
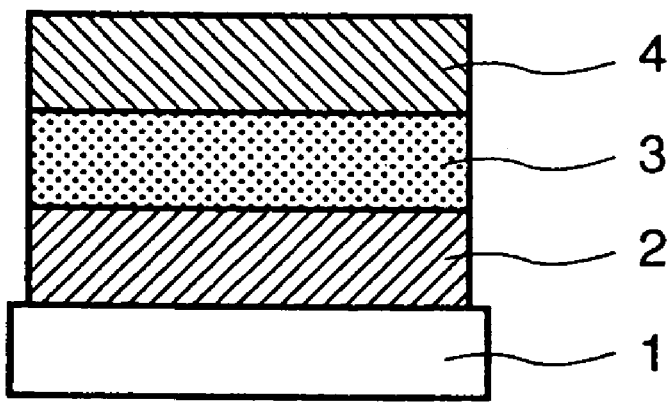
FIGS. 1 to 6 are respectively a schematic sectional view showing an embodiment of the organic luminescence device according to the present invention.

Hereinbelow, the present invention will be described more specifically.

The organic luminescence device according to the present invention comprises a pair of electrodes composed of an anode and a cathode and at least one organic luminescence function layer disposed between the pair of electrodes. Examples of such an organic luminescence function layer may include a luminescence layer, a hole transport layer, an electron transport layer, a hole injection layer and a hole/exciton blocking layer.

In the present invention, the above-mentioned at least one organic luminescence function layer may preferably have one to five layer structures specifically described hereinafter with reference to FIGS. 1–6.

At least one organic luminescence function layer described above includes at least one layer comprising a fused polynuclear compound represented by any one of the above-mentioned formulas (I) to (VII).

Specific examples of $R_1$ to $R_{26}$ and $Ar_1$ to $Ar_{24}$ in the formulas (I) to (VII) for the fused polynuclear compound used in the present invention will be shown below.

[For $R_1$ to $R_{24}$]

Examples of alkyl group may include methyl, ethyl, n-propyl, iso-propyl, n-butyl, tert-butyl and octyl.

Examples of aralkyl group may include benzyl and phenethyl.

Examples of aryl group may include phenyl, biphenyl and terphenyl.

Examples of heterocyclic group may include thienyl, pyrrolyl, pyridyl, quinolyl, carbazolyl, oxazolyl, oxadiazolyl, thiazolyl, thiadiazolyl, terthienyl and terpyrrolyl.

Examples of substituted amino group may include dimethylamino, diethylamino, dibenzylamino, diphenylamino, ditolylamino and dianisolylamino.

$R_1$ to $R_{26}$ may be hydrogen atom or cyano group as described above.

Herein, the terms "aryl group" and "heterocyclic group" for $R_1$ to $R_{26}$ mean those free from a fused ring structure as in those for $Ar_1$ to $Ar_{24}$.

[For $Ar_1$ to $Ar_{24}$]

Examples of fused polynuclear aromatic group may include naphthyl, anthryl, phenanthryl, pyrenyl, tetracenyl, pentacenyl, fluorenyl, triphenylenyl and peryleniyl, more preferably those represented by the above-mentioned formulas (VIII) to (XIII).

Examples of fused polynuclear heterocyclic group may include acrydinyl and fluorenonyl.

Examples of substituents for the above-mentioned groups for $R_1$ to $R_{26}$ and $Ar_1$ to $Ar_{24}$ may include: alkyl groups such as methyl, ethyl and propyl; aralkyl groups such as benzyl and phenethyl; aryl groups such as phenyl, naphthyl, anthryl, phenanthryl, pyrenyl, tetracenyl, pentacenyl, and fluorenyl; heterocyclic groups such as thienyl, pyrrolyl and pyridyl; amino groups such as dimethylamino, diethylamino, dibenzylamino, diphenylamino, ditolylamino and dianisolylamino; alkoxy groups such as methoxy, ethoxy, propoxy and phenoxy; cyano group; and nitro group.

Hereinafter, the fused polynuclear compounds of the formulas (I) to (VII) used in the present invention will be shown specifically by their structural formulas (Example Compound Nos. 1 to 66) for the respective formulas (I) to (VII) but are not restricted to the following specific compounds.

Formula [I]

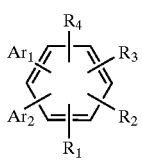

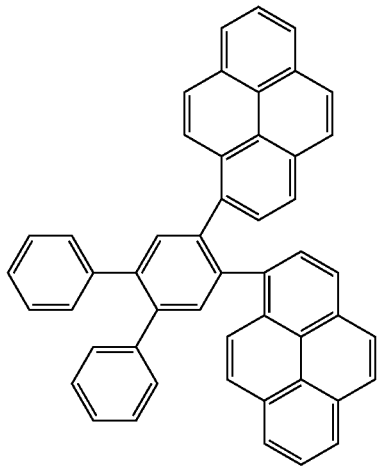

1

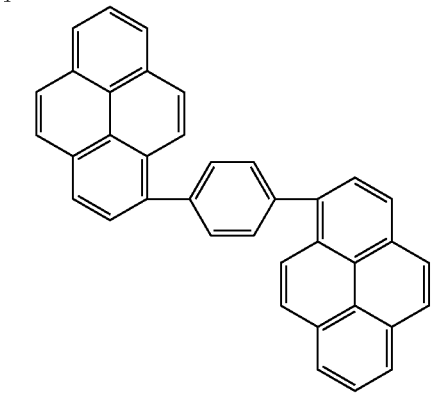

2

-continued
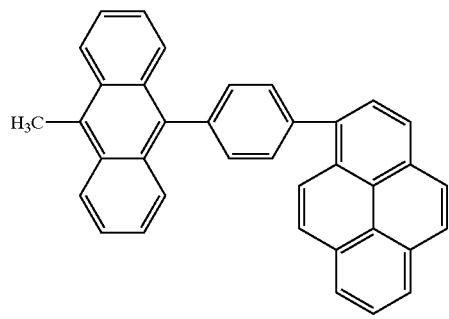
3
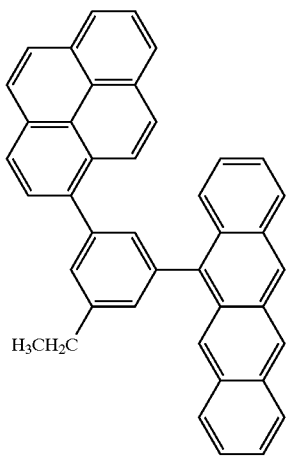
4
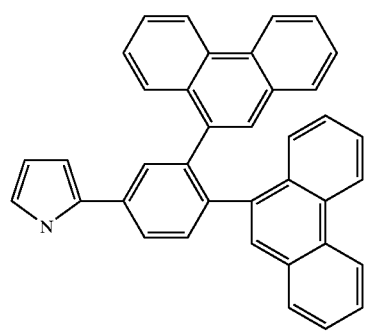
5
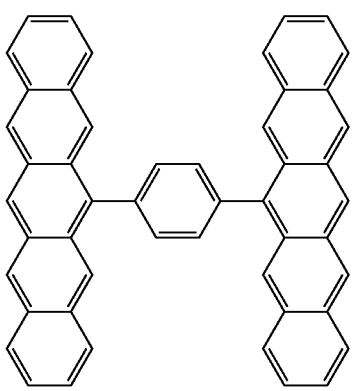
6
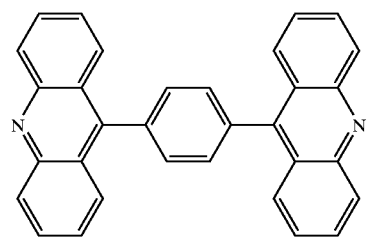
7
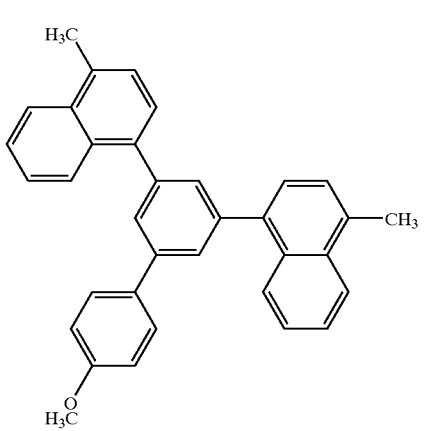
8
Formula [II]
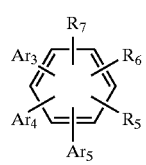

-continued
9
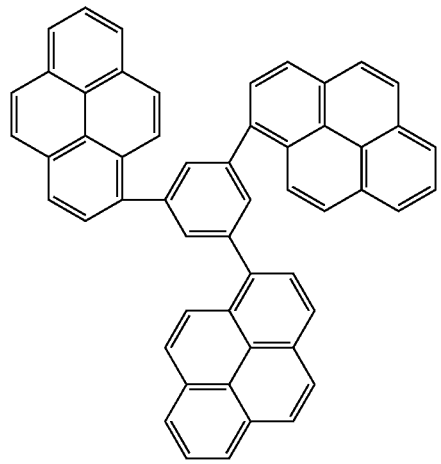
10
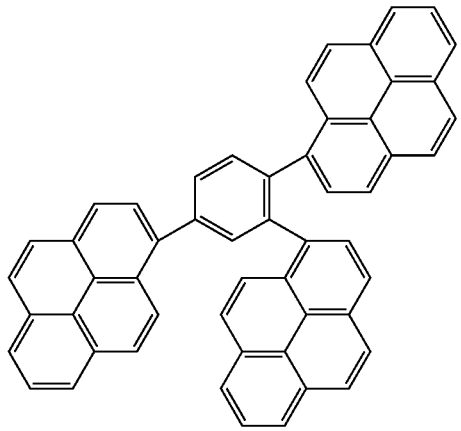
11
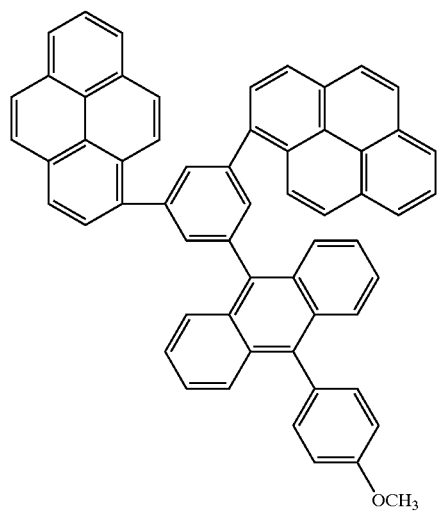
12
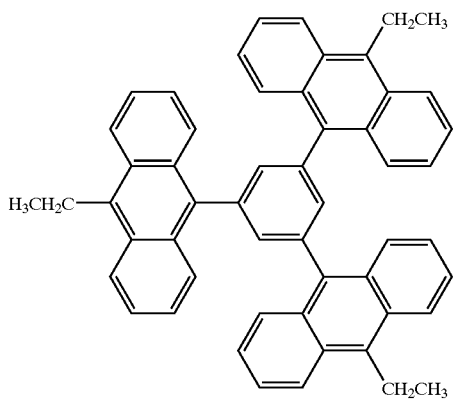
13
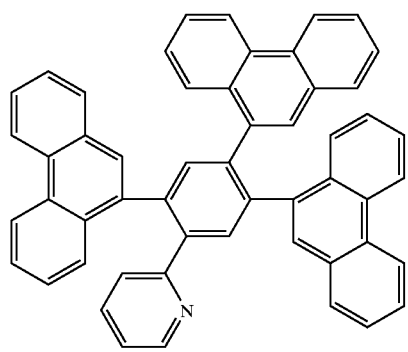
14
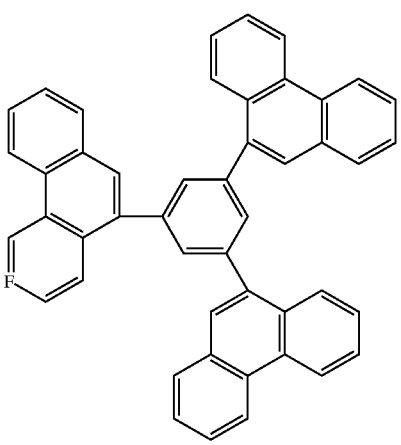

-continued
15
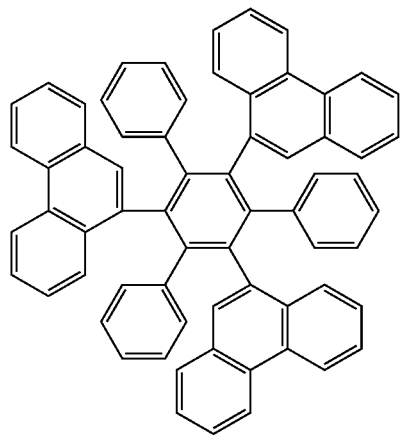
16
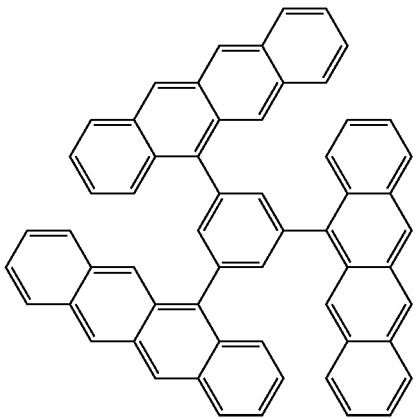
17
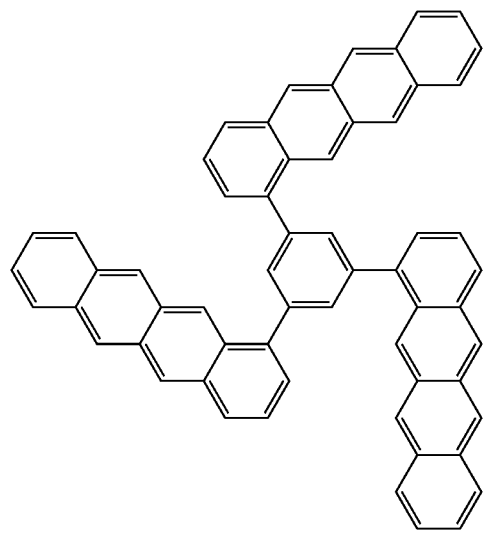
18
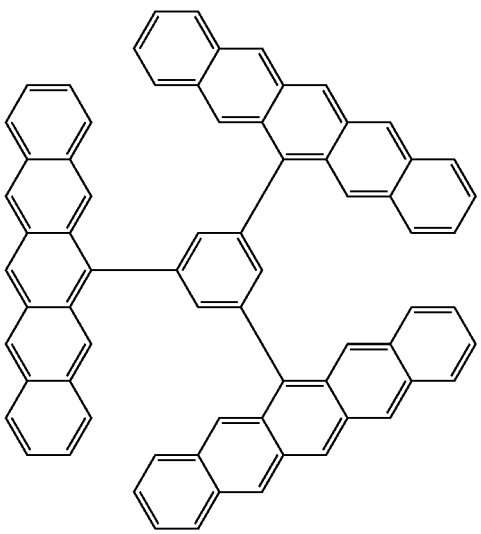
19
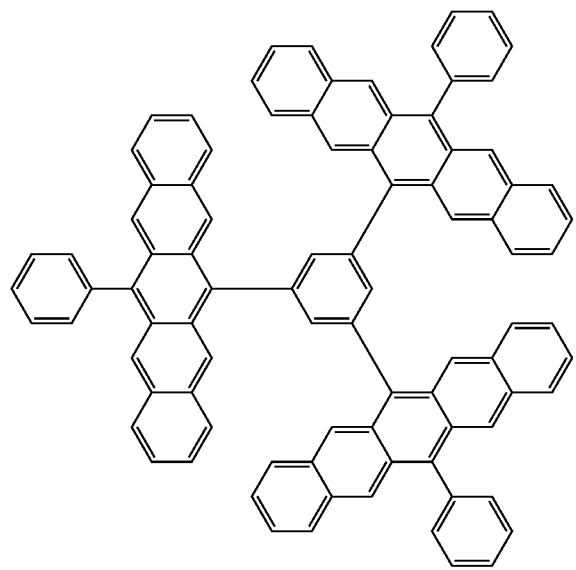
20
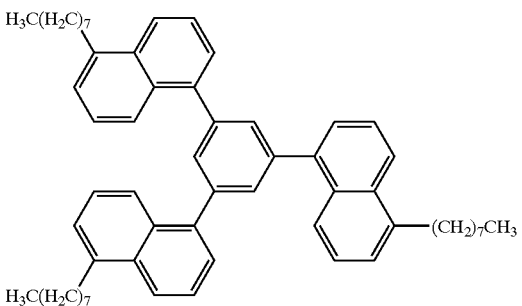

-continued
21
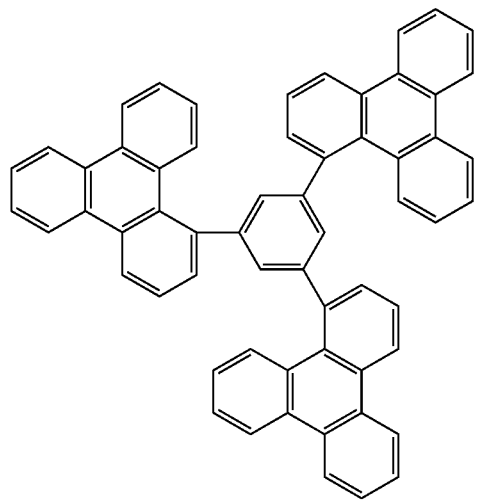
22
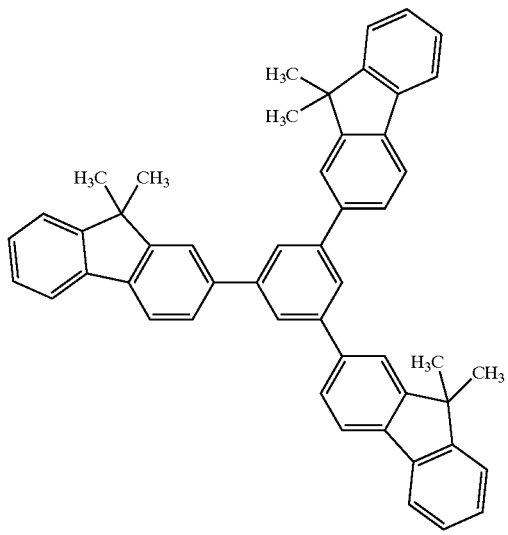
23
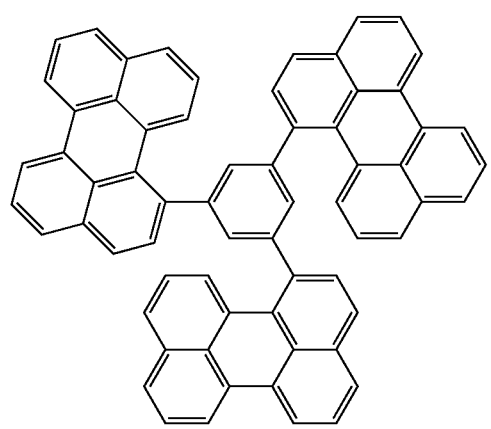
24
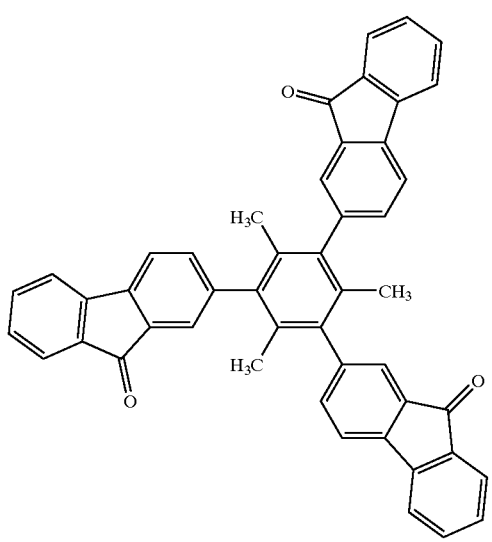
25
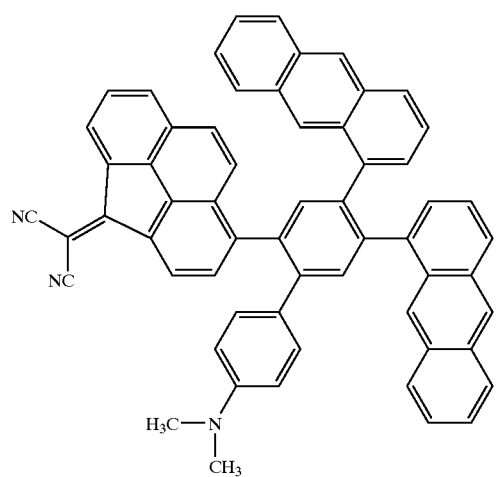
26
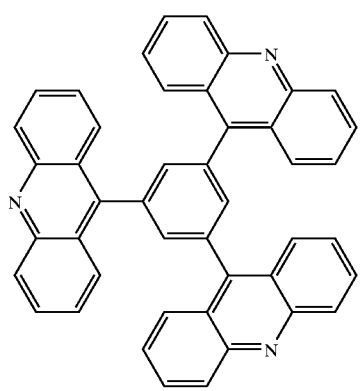

-continued
27
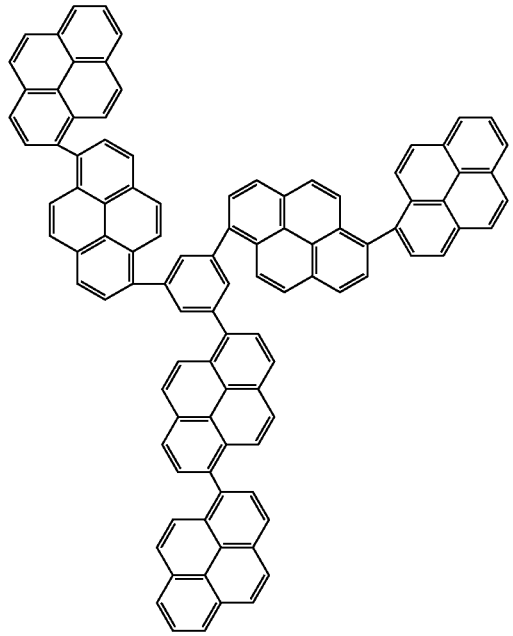
28
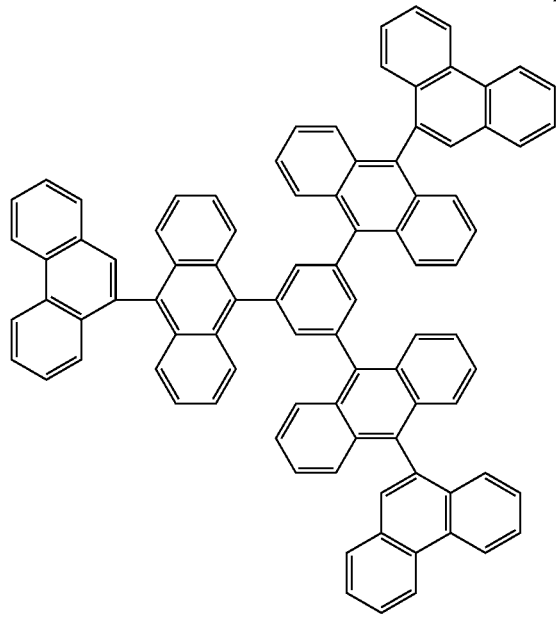
Formula [III]
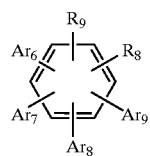
29
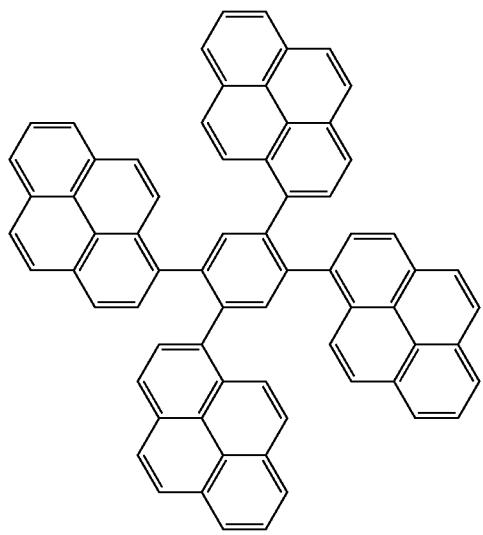
30
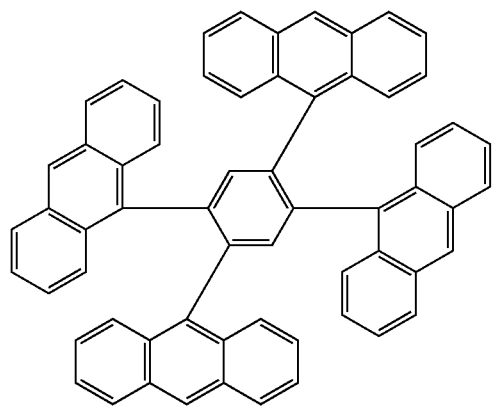

-continued
31
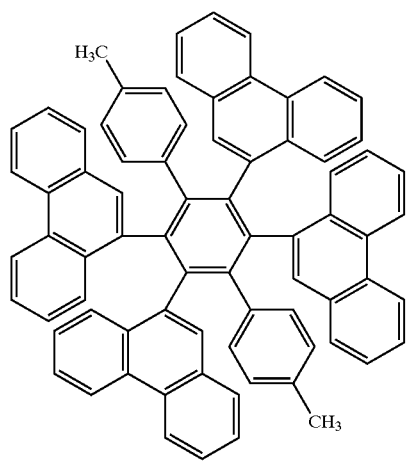
32
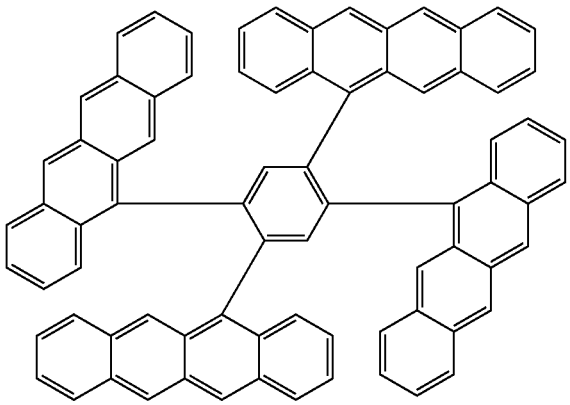
33
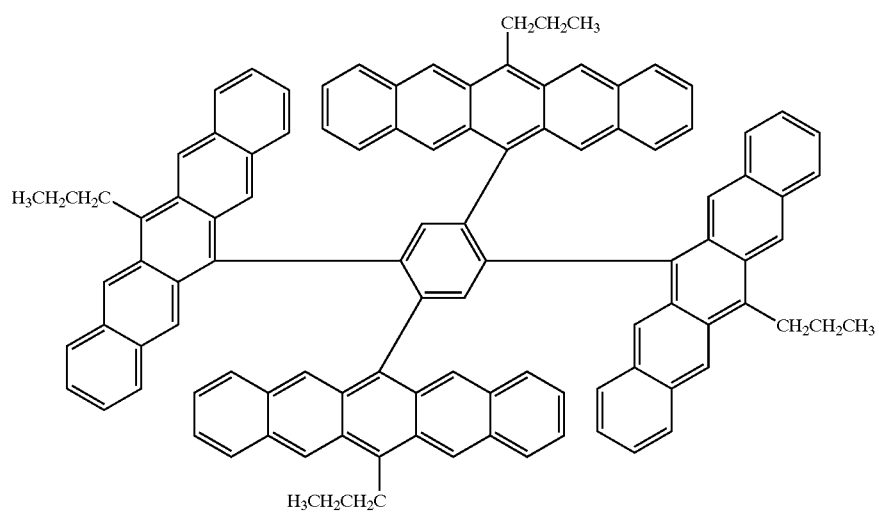
34
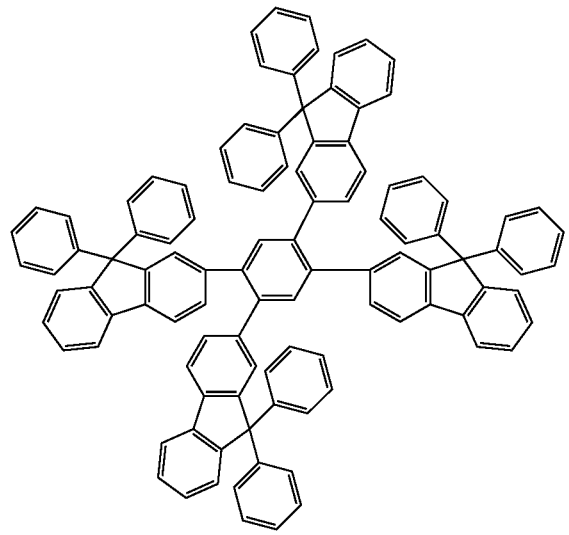
35
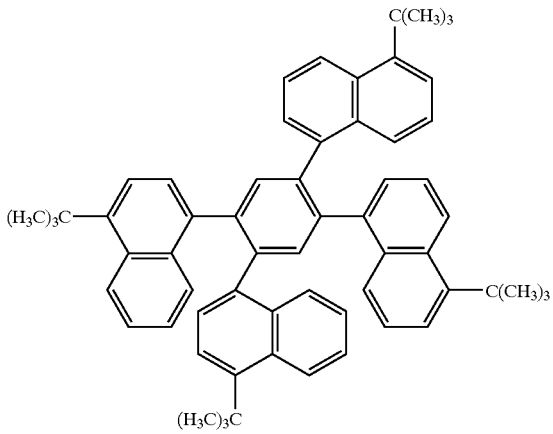

-continued
36
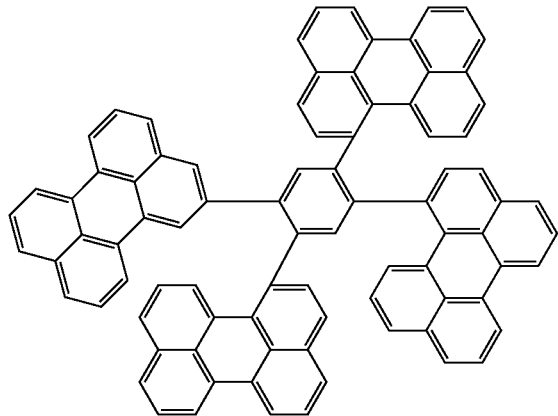
Formula [IV]
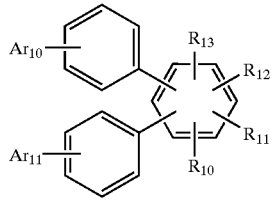
37
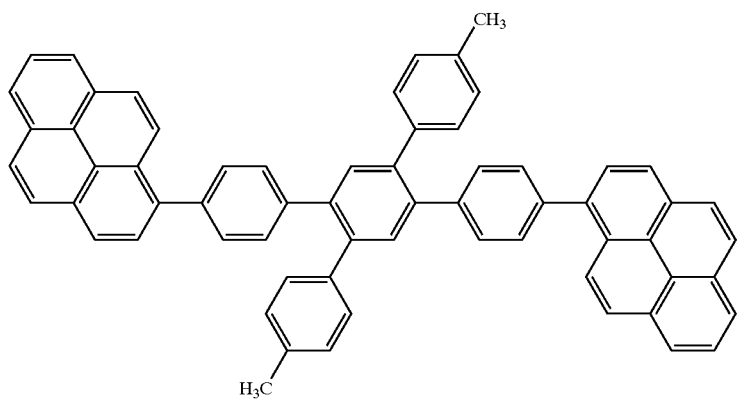
38
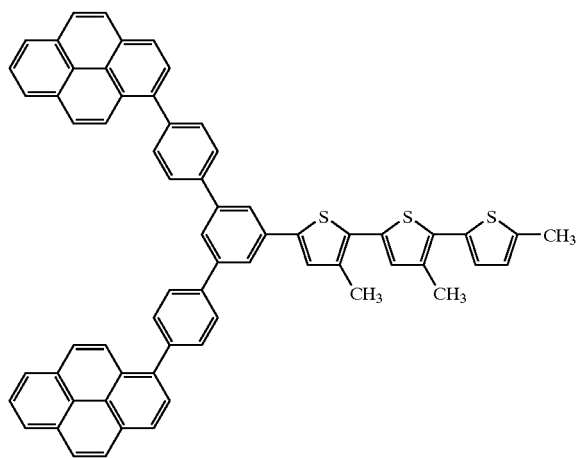
39
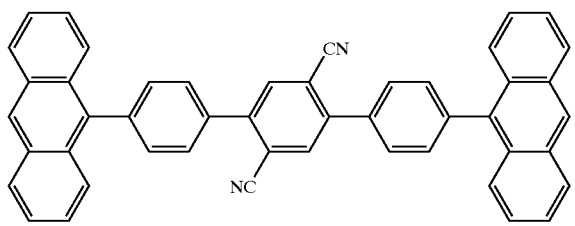

-continued
40
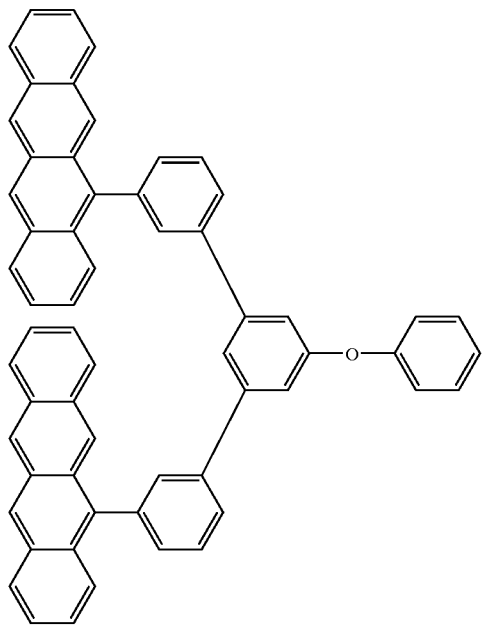
41
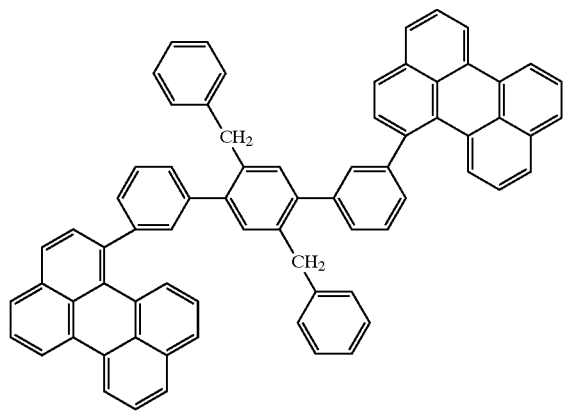
42
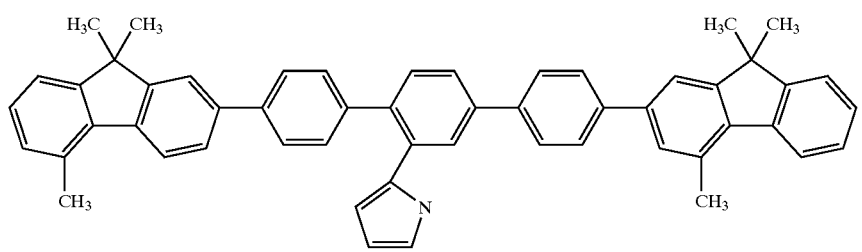
43
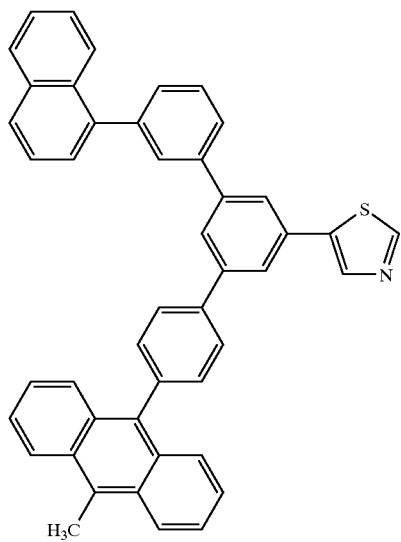

-continued
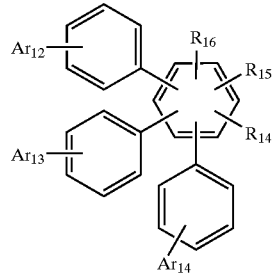
Formula [V]
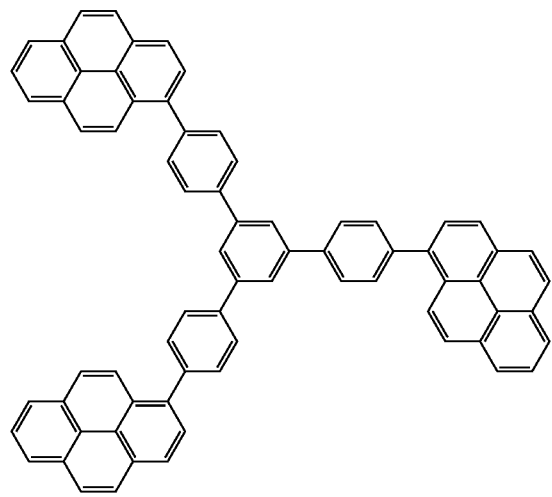
44
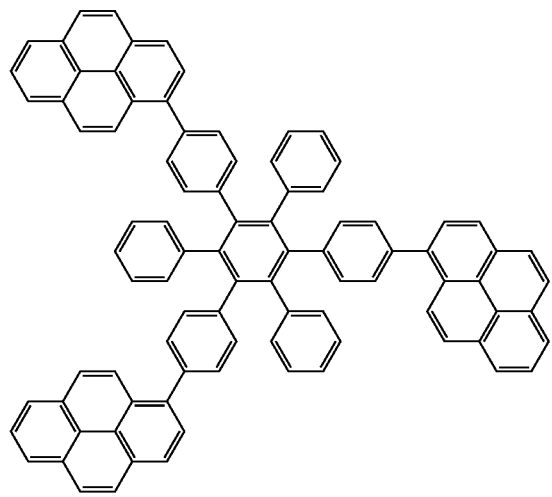
45
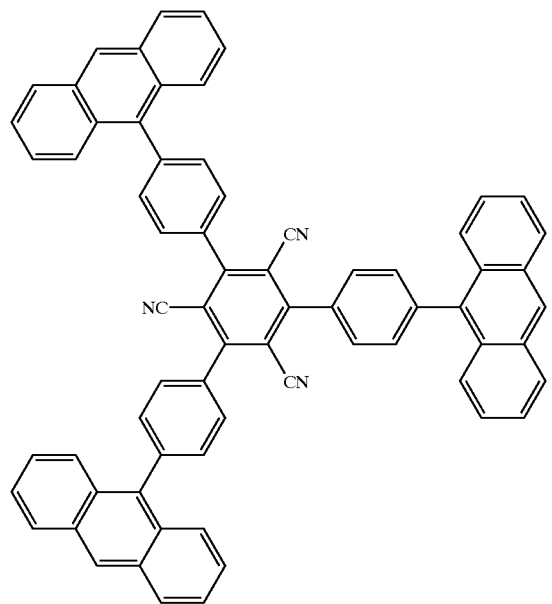
46
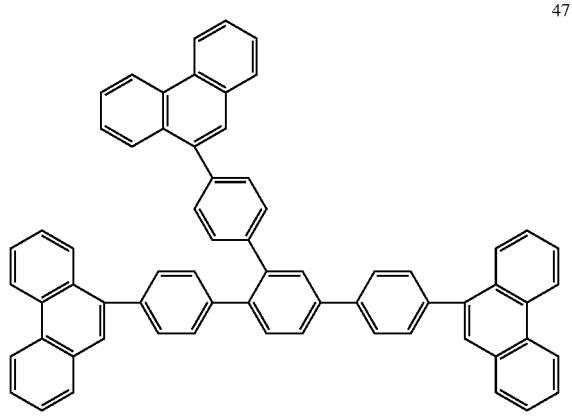
47

-continued
48
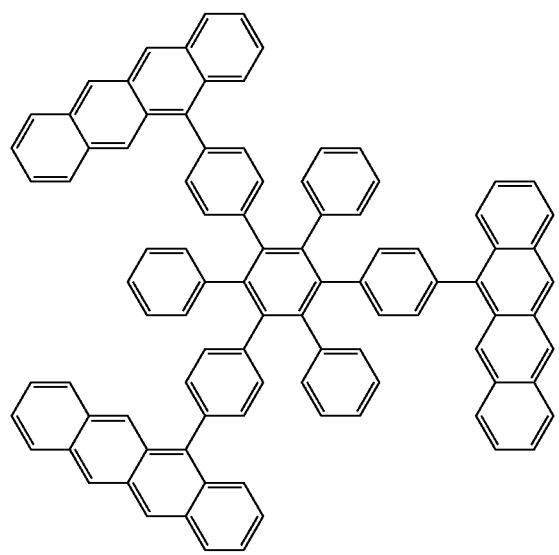
49
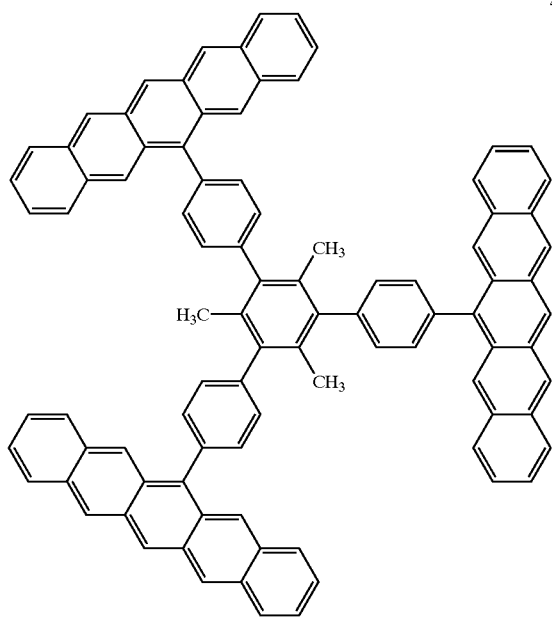
50
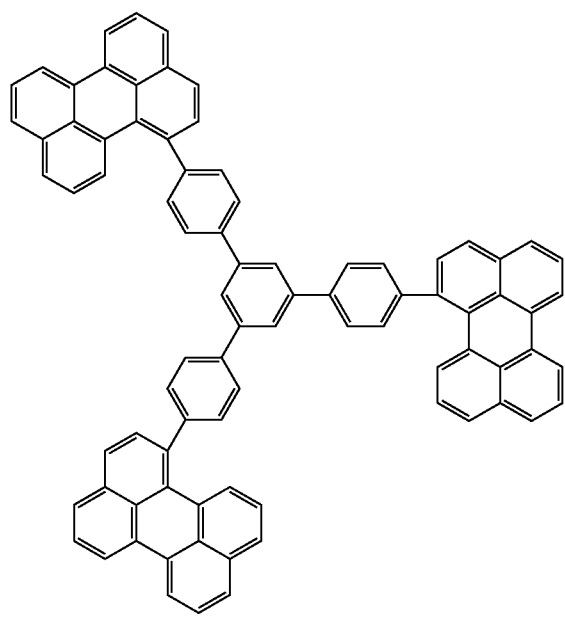
51
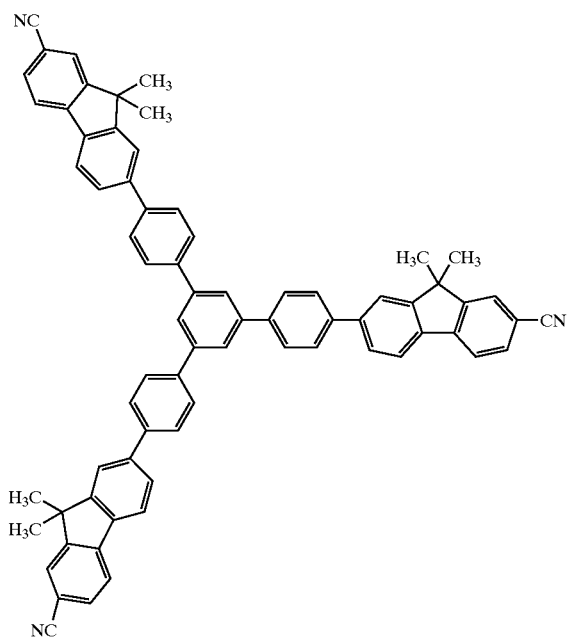
Formula [VI]
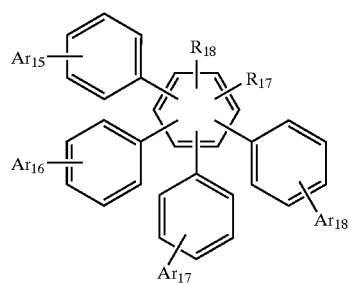

-continued
52 53 54 55
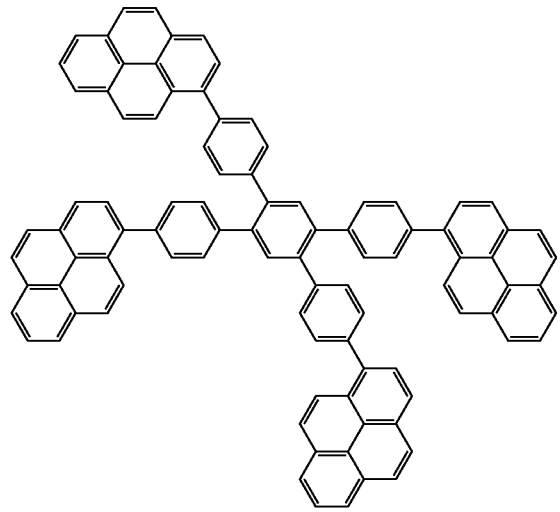

-continued
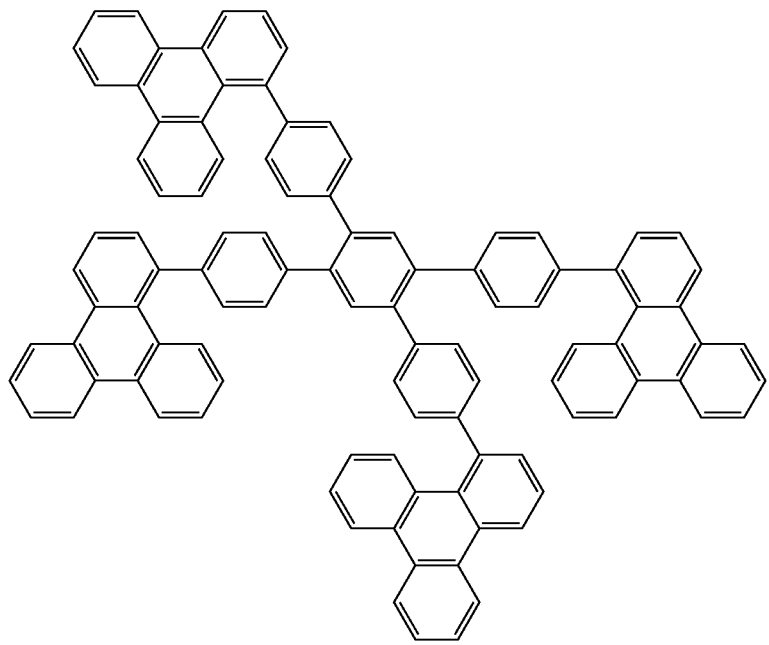
56
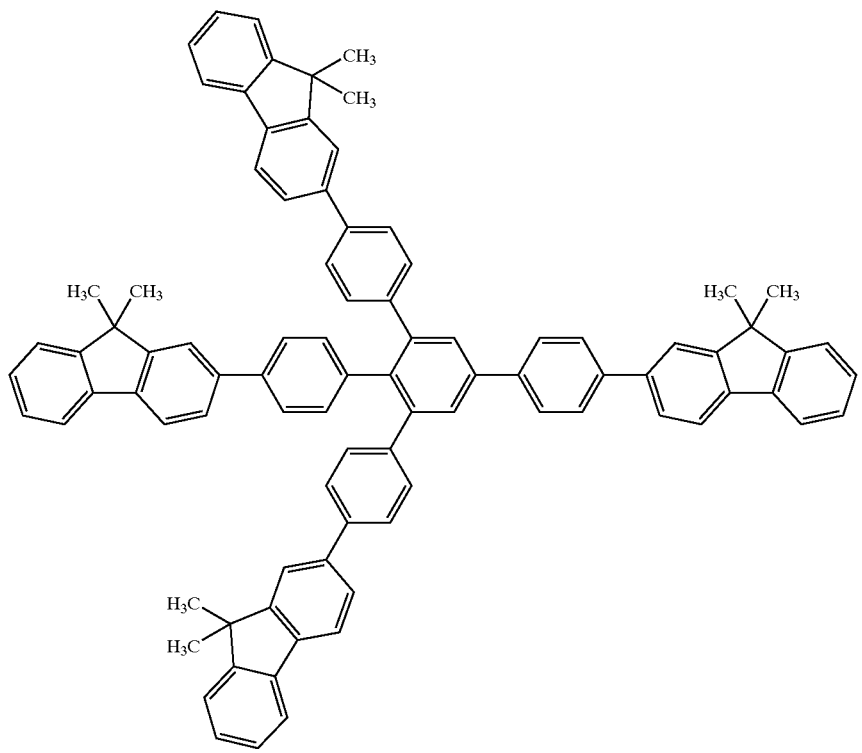
57

Formula [VII]
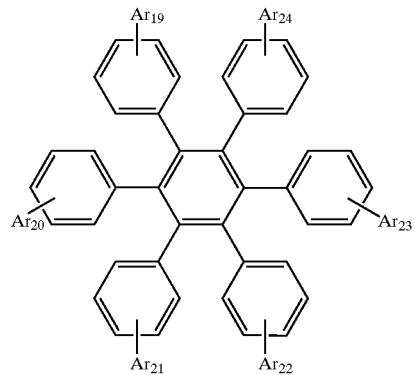
58
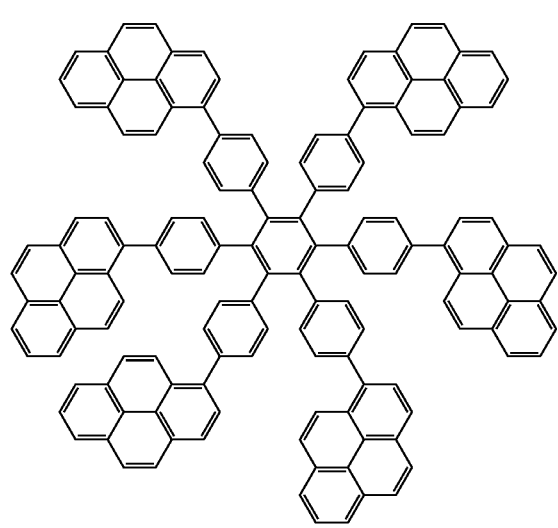
59
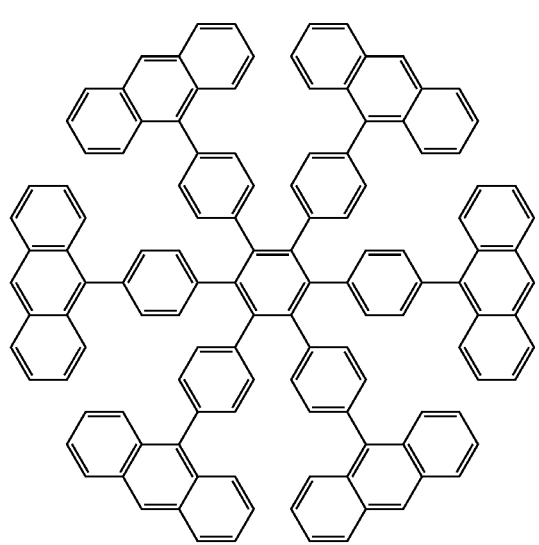
60
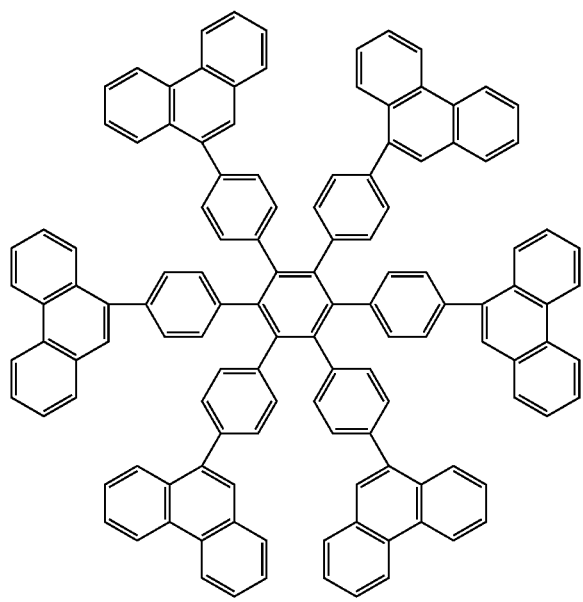
61
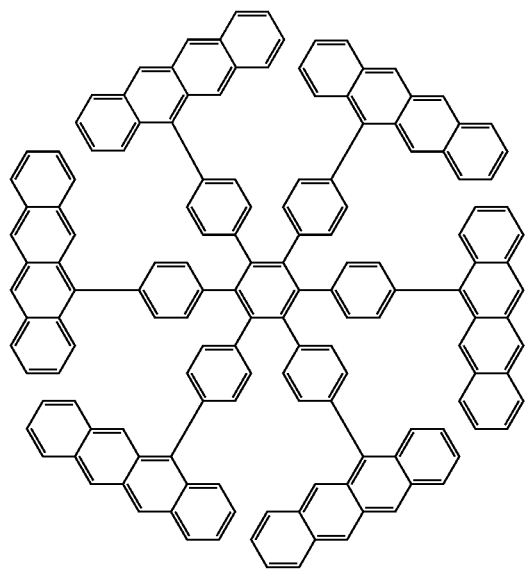

-continued
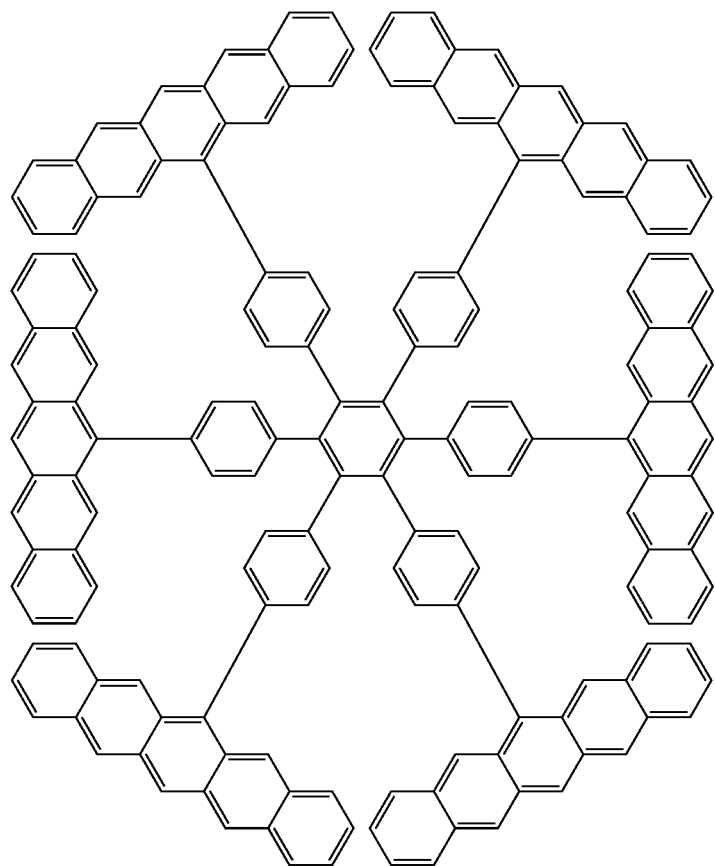
62
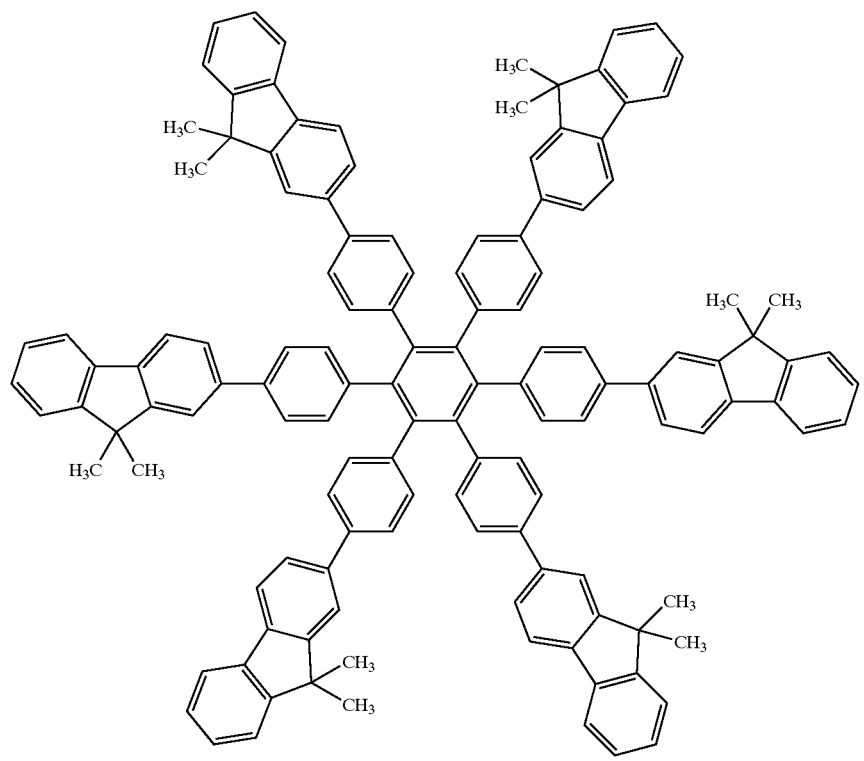
63

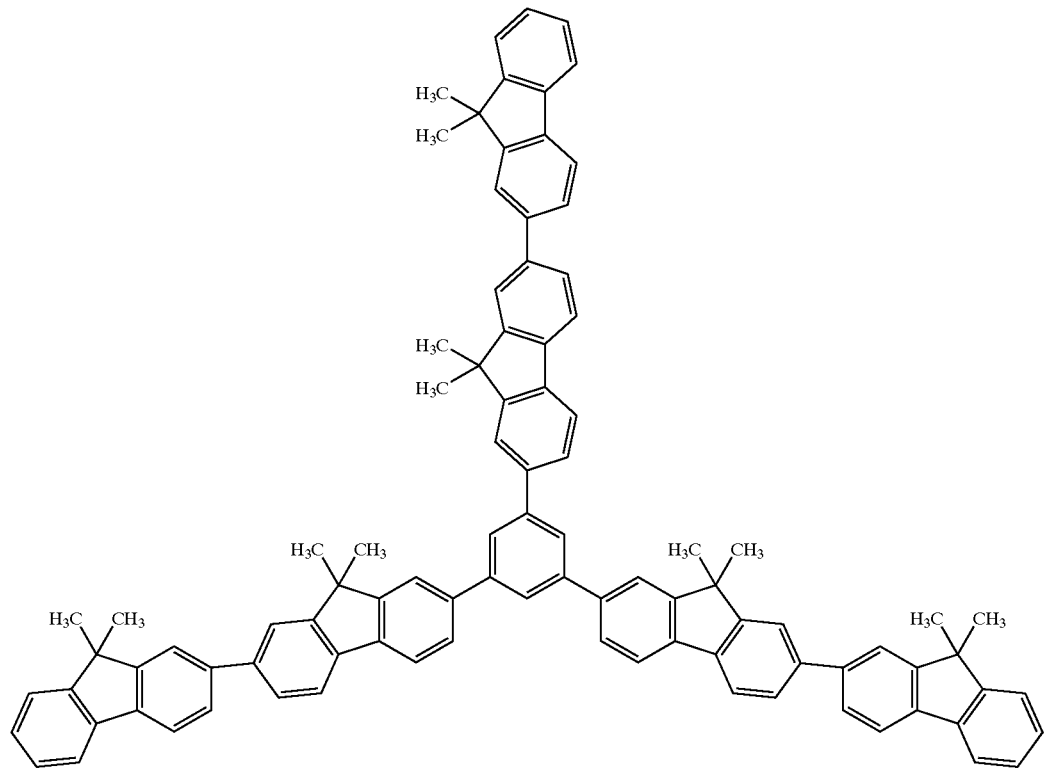
64
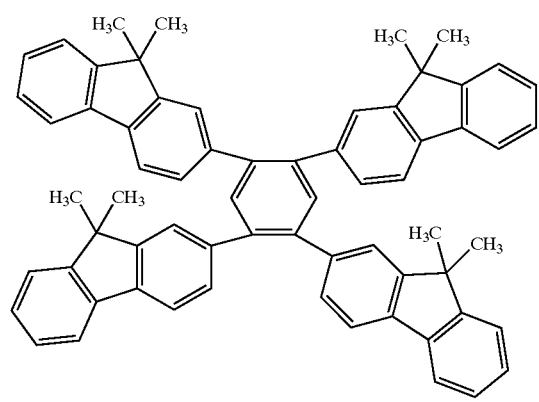
65

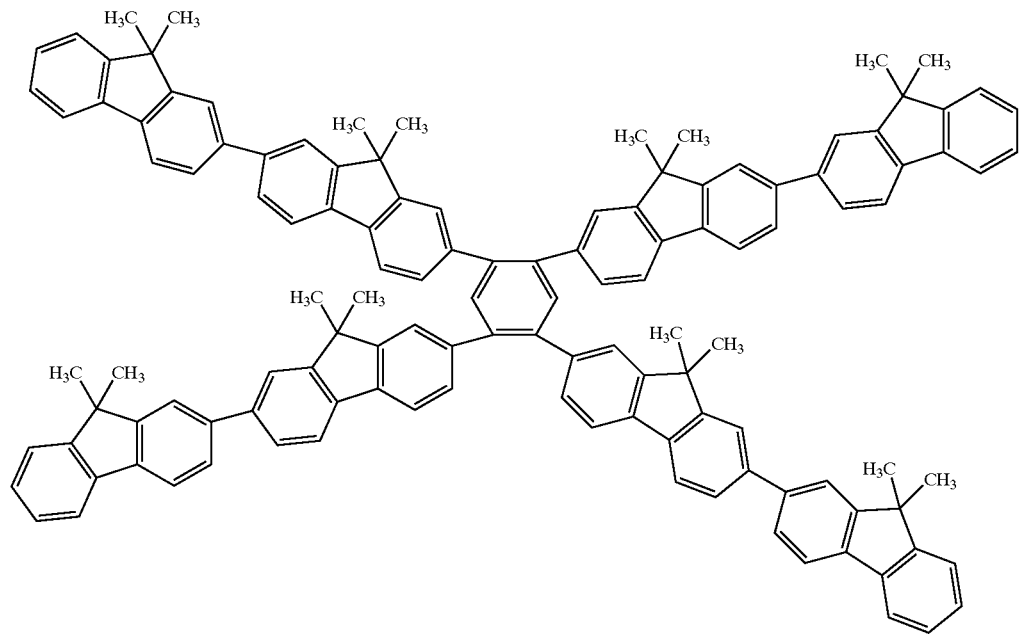

66

The fused polynuclear compounds of the formulas (I) to (VII) used in the present invention may be synthesized through ordinary processes including Suzuki Coupling process using a palladium catalyst (e.g., "Chem. Rev.", 95, 2457–2483 (1995)), Yamamoto process using a nickel catalyst (e.g., "Bull. Chem. Soc. Jpn." 51, 2091 (1978) and a process using an aryl tin compound (e.g., "J. Org. Chem.", 52, 3296 (1987)).

The fused polynuclear compound of the formulas (I) to (VII) used in the present invention is an excellent organic luminescence function material in terms of electron transfer performance, luminescence performance and durability, thus being a material suitable for an electron transport layer and/or a luminescence layer. Further when an organic luminescence function layer is formed by vacuum (vapor) deposition or wet coating using an appropriate solvent, the resultant organic luminescence function layer is less liable to cause crystallization, thus being excellent in stability with time.

In the present invention, as described above, the organic luminescence function layer disposed between the pair of electrodes (anode and cathode) may be formed in a plurality of organic compound layers including at least one layer thereof comprising the above-mentioned fused polynuclear compound of the formulas (I) to (VII). Further, such at least one layer may preferably functions as an electron transport layer or a luminescence layer.

Each of the organic compound layers (organic luminescence function layers) may preferably be formed-in a thickness of at most 10 μm, more preferably at most 0.5 μm, most preferably 0.01–0.5 μm.

Hereinbelow, layer structures of the organic luminescence device according to the present invention will be described specifically with reference to FIGS. 1 to 6 each illustrating an embodiment thereof.

Referring to FIGS. 1–6 the respective organic luminescence devices basically include a substrate 1, an anode 2 disposed on the substrate 1, one or more organic luminescence function layer disposed on the anode 2, and a cathode 4 disposed on the one or more organic luminescence function layer.

In an embodiment shown in FIG. 1, the organic luminescence function layer is composed of a single layer exhibiting multifunctional performances in terms of a hole transport ability, an electron transportability and a luminescence performance. These performances may be given by using a single multifunctional compound or by mixing the respective functional materials in a single layer.

Figure 2:
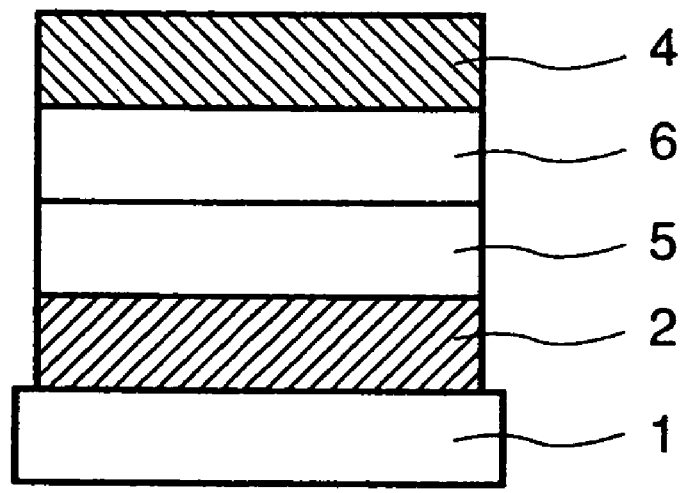

In another embodiment shown in FIG. 2, the organic luminescence function layer is composed of a hole transport layer 5 disposed on the anode 2 and an electron transport layer 6 disposed on the hole transport layer 5. In this embodiment, a luminescent material also exhibits either one or both of a hole transport performance and an electron transport performance and is used in combination with a hole transport material free from a luminescence performance or an electron transport material free from a luminescence performance. In this embodiment, either one of the hole transport layer 5 and the electron transport layer 6 also functions as in the luminescence layer.

Figure 3:
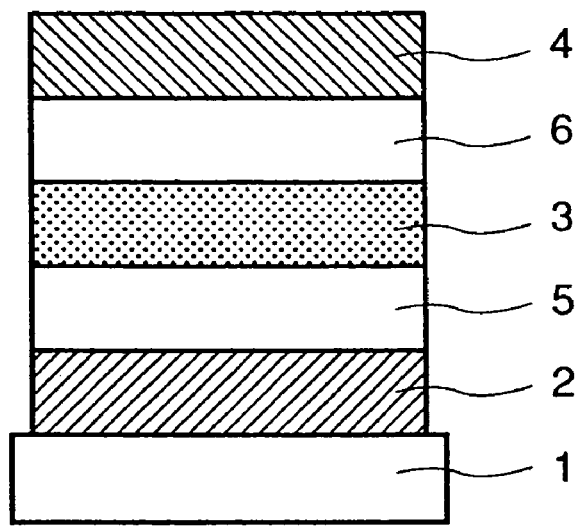

In another embodiment shown in FIG. 3, the organic luminescence function layer is composed of three layers consisting of a hole transport layer 5, a luminescence layer 3 and an electron transport layer 6 disposed in this order on the anode 2. In this embodiment, carrier (hole/electron) transport performances and luminescence performance are functionally separated into the three layers which may appropriately be formed by using respective functional materials exhibiting a hole transport performance, an electron transport performance and a luminescence performance. As a result, it is possible to allow not only an increased latitude in selection of materials but also use of various compounds different in emission wavelength, thus resulting in a variety of emission hues. Further, it also becomes possible to effectively confining respective carriers or excitons in the luminescence layer 3 thus improving a luminescence-efficiency.

Figure 4:
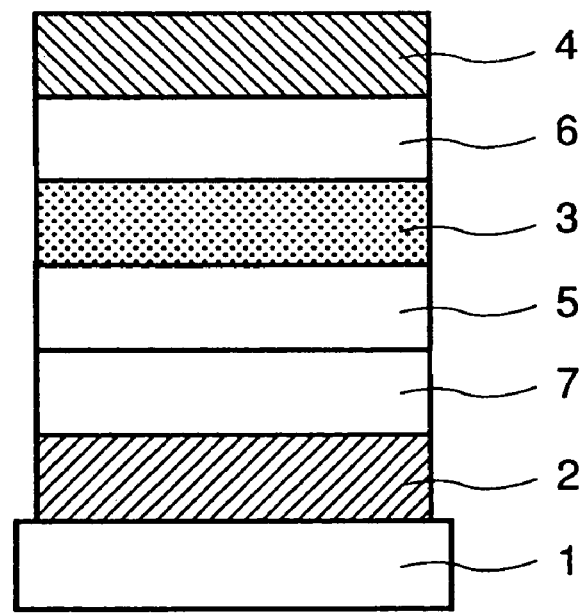

FIG. 4 shows another embodiment of the organic luminescence device of the present invention. Referring to FIG. 4, the organic luminescence device has four layers as the organic luminescence function layers including three functional layers similar to those (hole transport layer 5, luminescence layer 3 and electron transport layer 6) shown in FIG. 3 and a hole injection layer 7 disposed between the anode 2 and the hole transport layer 5. The use of the hole injection layer 7 is effective in improving adhesive properties between the anode 2 and the hole transport layer 5 or hole injection performance, thus resulting in luminescence at a low applied voltage.

Figure 5:
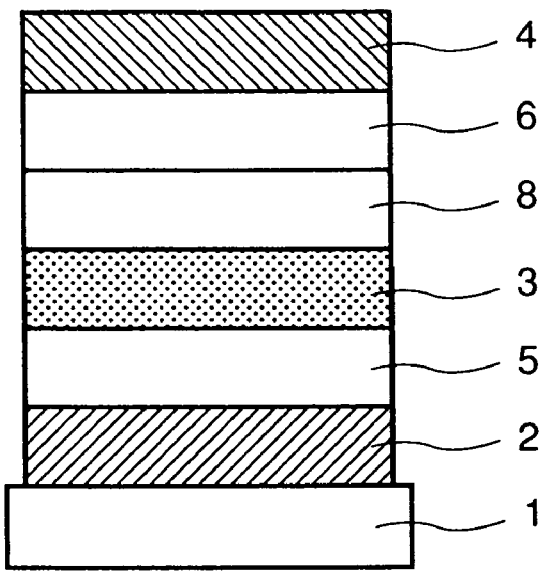
Figure 6:
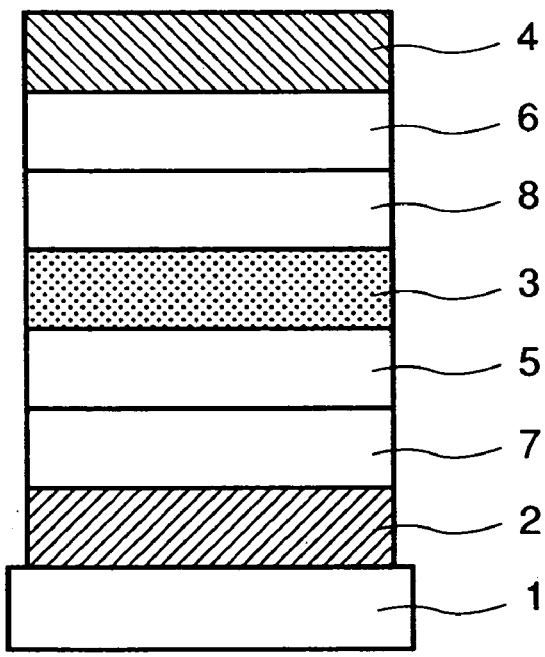

FIGS. 5 and 6 show other embodiments similar to those shown in FIGS. 3 and 4, respectively, except that a hole (or exciton) blocking layer 8 for blocking passing of holes or excitons to the anode side is disposed between the electron transport layer 6 and the luminescence layer 3. In these embodiments, by using a compound exhibiting a very high ionization potential in the hole blocking layer 8, a resultant luminescence efficiency is effectively improved.

The layer structure of organic luminescence device of the present invention using the above-mentioned fused polynuclear compound is not restricted to those described above with reference to FIGS. 1–6 illustrating basic device structures of the organic luminescence device of the present invention.

For example, the layer structure of the organic luminescence device according to the present invention may be modified by additionally forming an insulating layer, an adhesive layer or an interference layer at a boundary between an electrode and an organic luminescence function layer. Further, the hole transport layer 5 may be composed of two layers different in ionization potential.

The fused polynuclear compound used in the present invention (represented by any one of the formulas (I) to (VII)) may preferably be used as a material suitable for the electron transport layer and/or the luminescence layer but may be used in combination with known hole transport compounds, luminescent compounds and/or electron transport compounds shown below.

Hole Transport Material

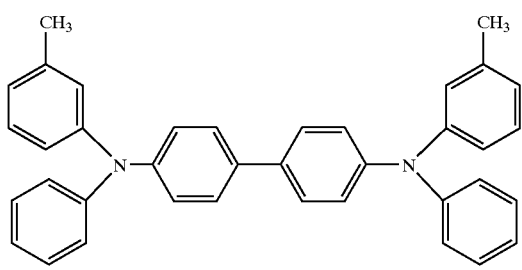

TPD

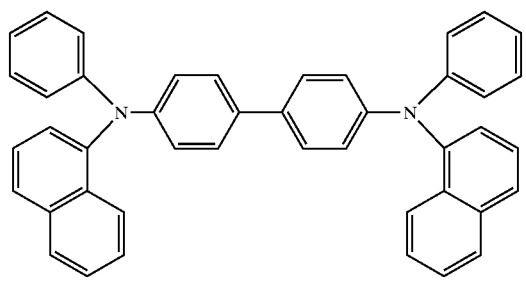

a-NPD

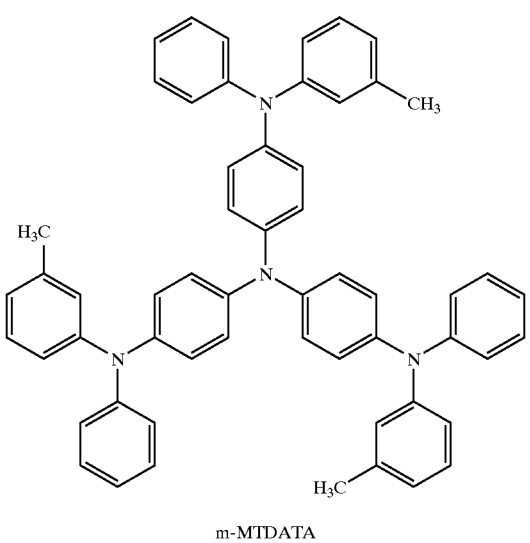

m-MTDATA

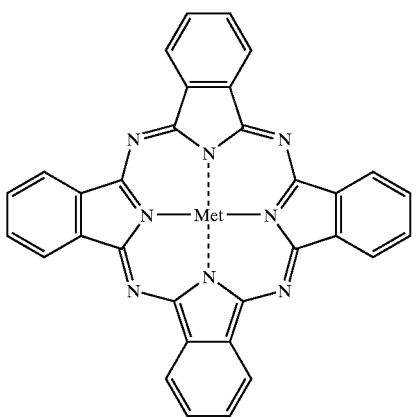

Met-Pc
Met = Cu, Mg, AlCl, TiO$_2$, SiCl$_2$, etc.

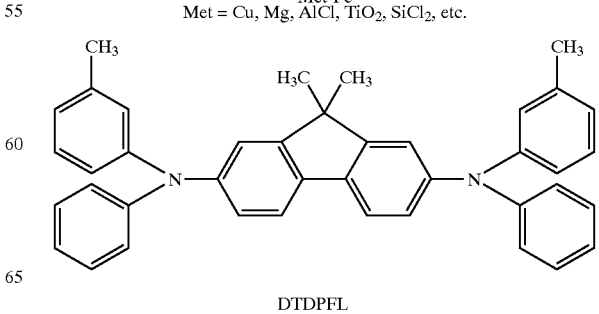

DTDPFL

-continued
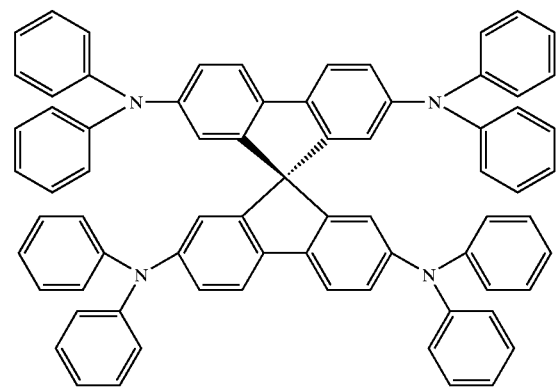
spiro-TPD
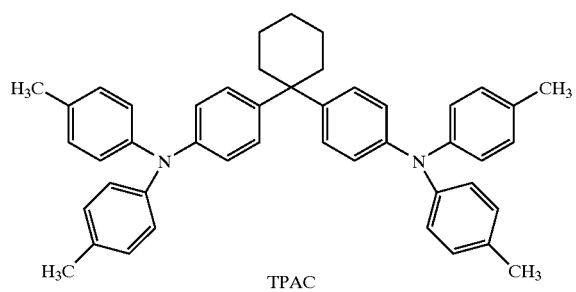
TPAC
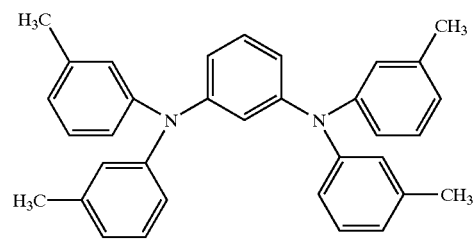
PDA
Electron Transport Luminescence Material
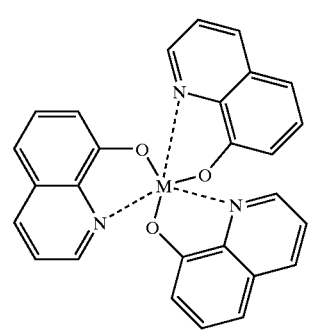
M = Al, Ga
-continued
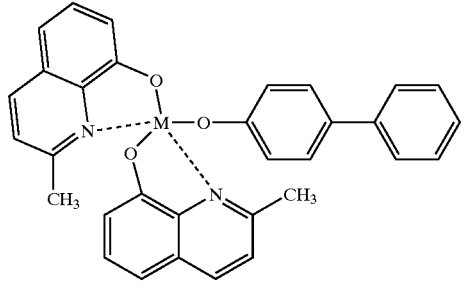
M = Al, Ga
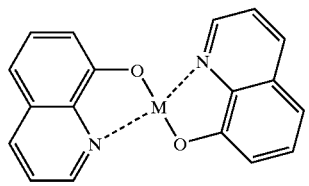
M = Zn, Mg, Be
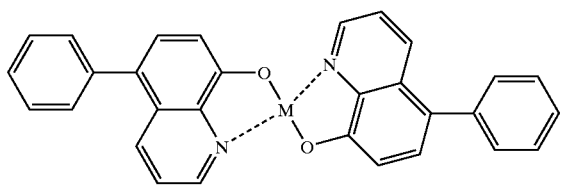
M = Zn, Mg, Be
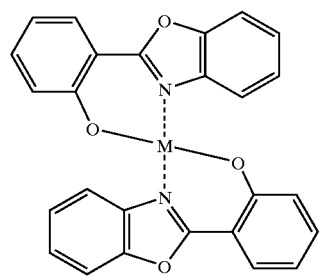
M = Zn, Mg, Be
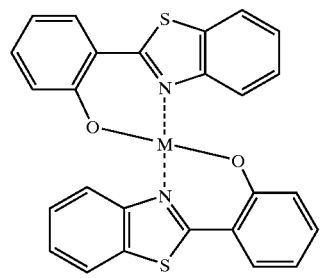
M = Zn, Mg, Be -continued
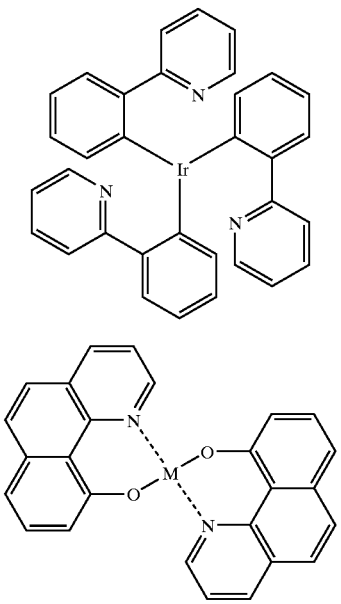
M = Zn, Mg, Be
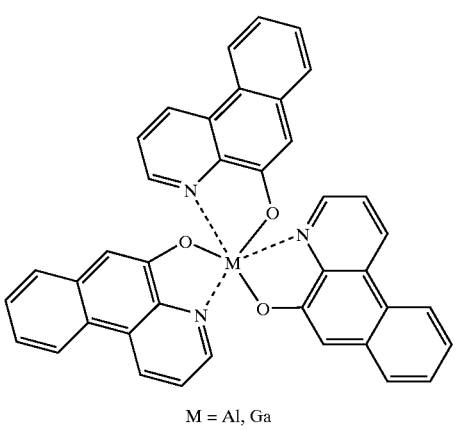
M = Al, Ga
Luminescence Material
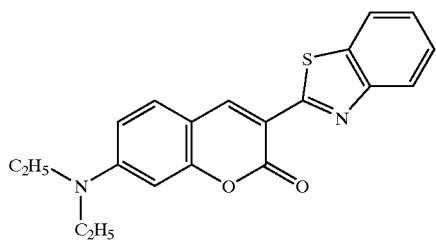
Coumarin 6
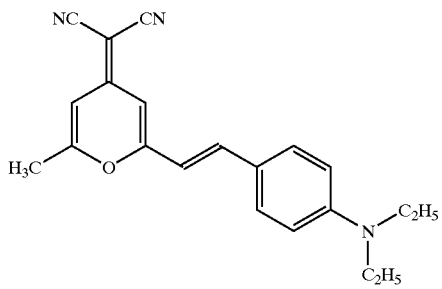
DCM-1
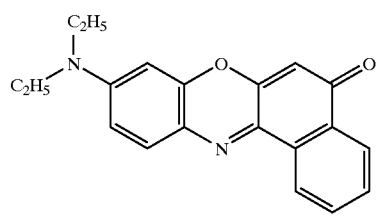
Nile red
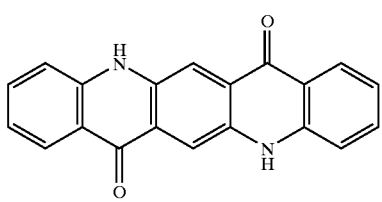
Quinacridone
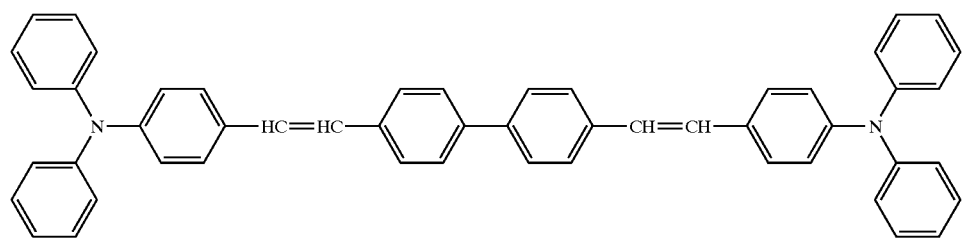
DPABVi -continued
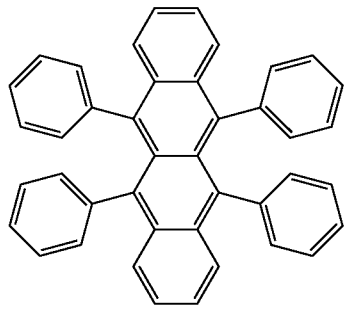
Rubrene
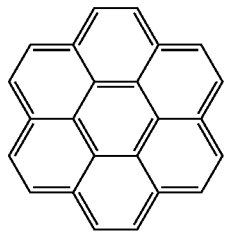
Coronene
Luminescence Layer Matrix (Host) Material and Electron Transport Material
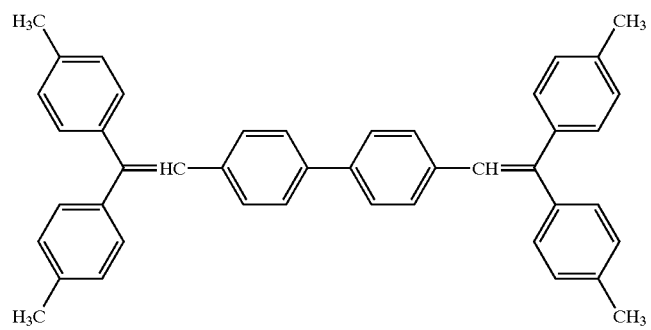
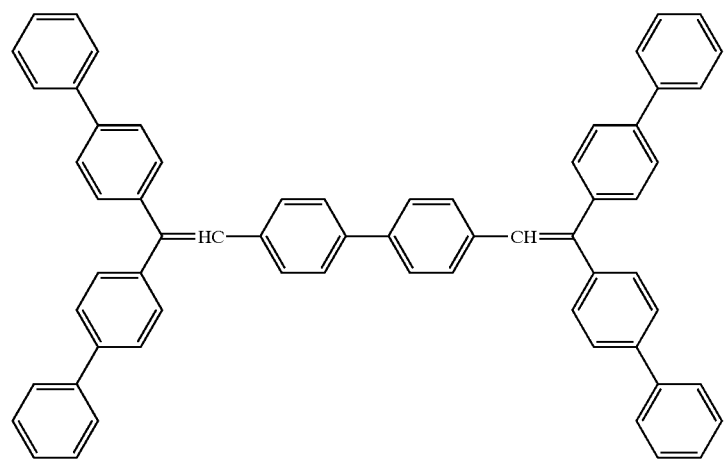
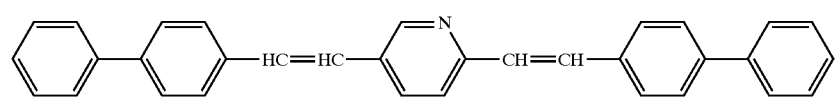

-continued
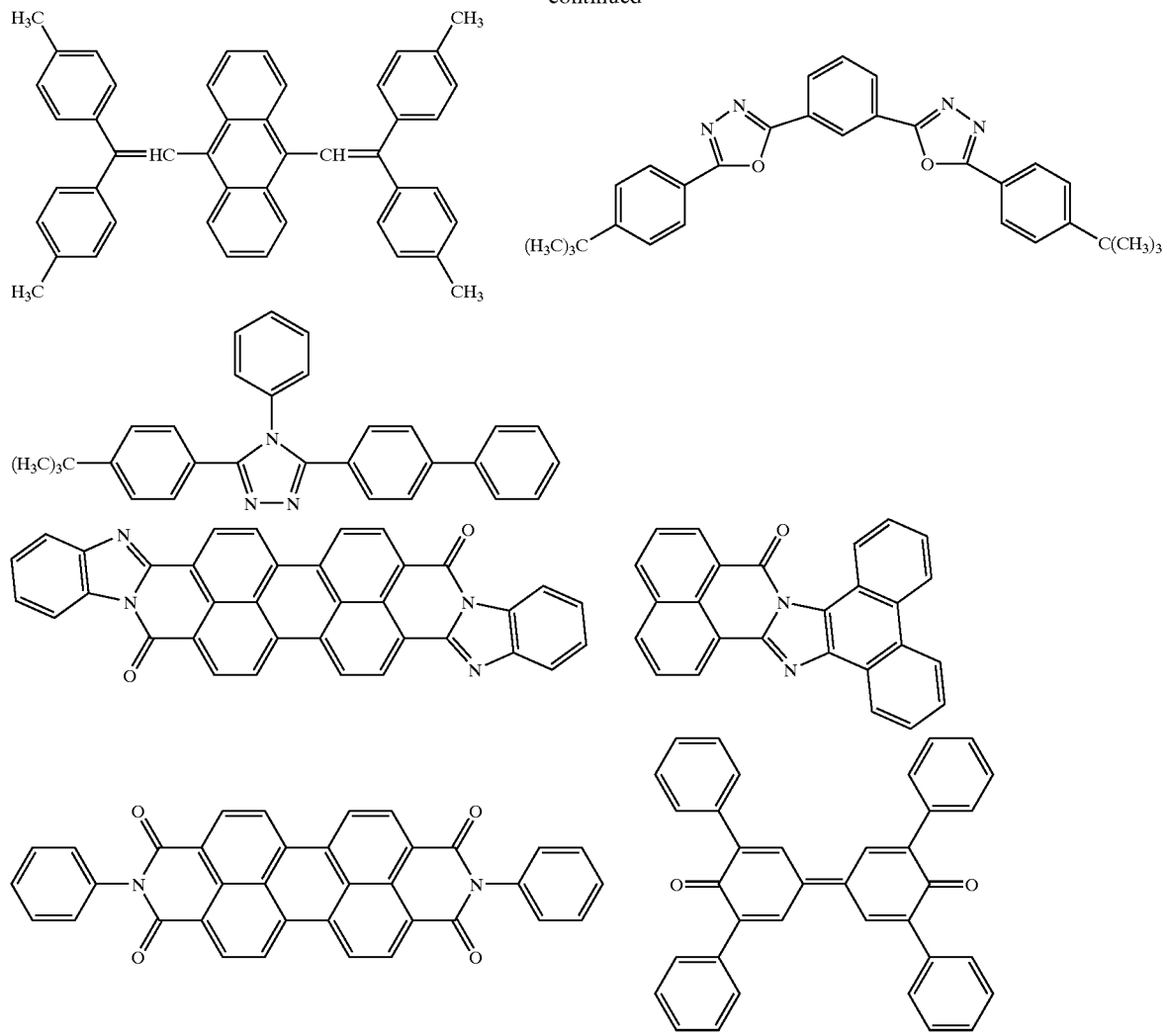
Polymer-type Hole Transport Material
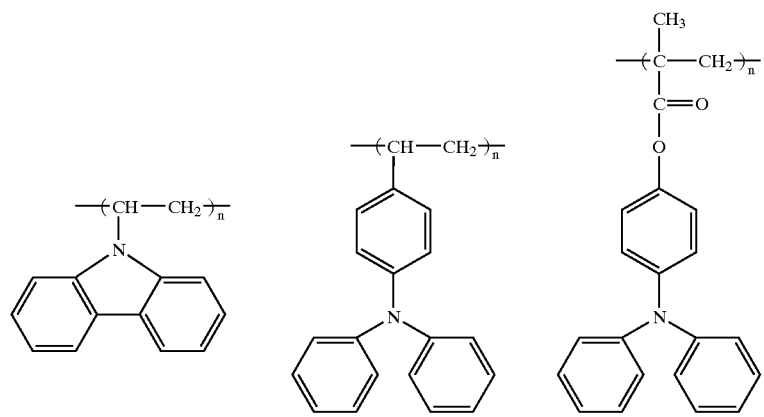
PVCz　　　DPA-PS　　　TPA-PMMA

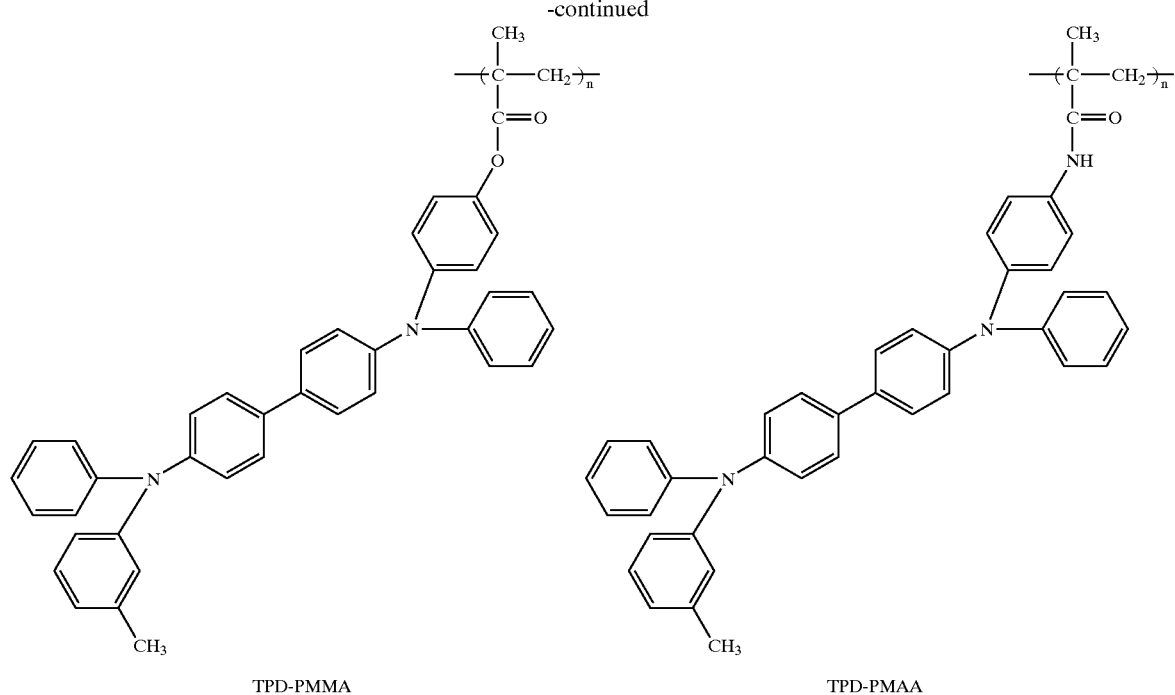
TPD-PMMA    TPD-PMAA
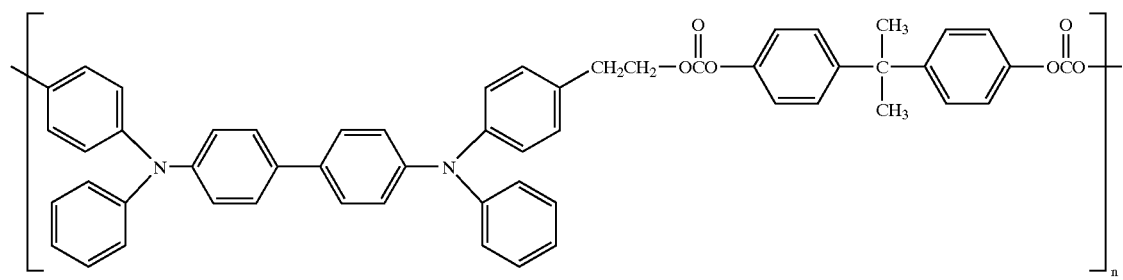
TPD-PCA
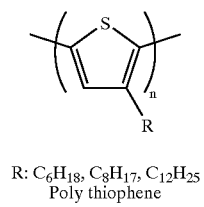
R: $C_6H_{18}$, $C_8H_{17}$, $C_{12}H_{25}$
Poly thiophene
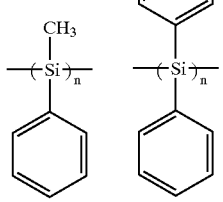
Poly silicone
Polymer-type Luminescence Material and Charge Transport Material
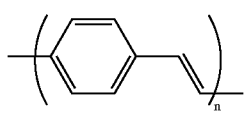
-continued
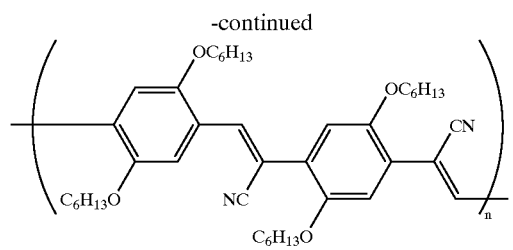

-continued

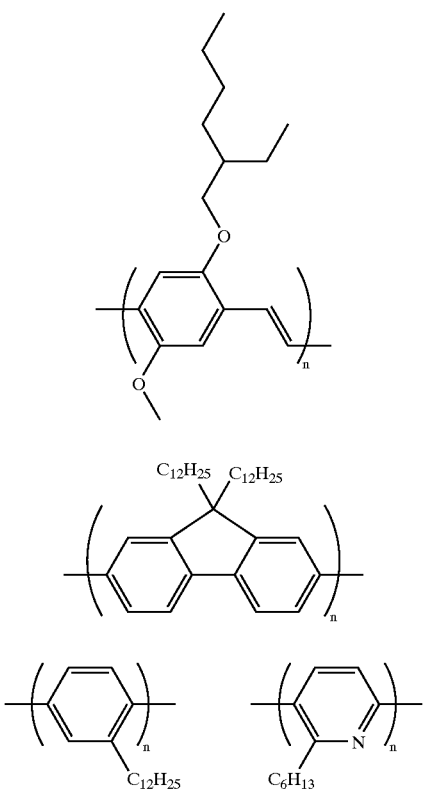

In the organic luminescence device according to the present invention, a layer of the fused polynuclear compound represented by the formulas (I) to (VII) and other layers comprising organic compounds may generally be formed in a thin film by vacuum deposition or wet coating using an appropriate solvent for dissolving such organic compounds (including the fused polynuclear compound). Particularly, in the case of using the wet coating, it is also possible to form a film in combination with an appropriate binder resin.

The binder resin may appropriately be selected from various known binder resins. Examples of the binder resin may include: polyvinyl carbazole, polycarbonate resin, polyester resin, polyarylate resin, polystyrene resin, acrylic resin, methacrylic resin, butyral resin, polyvinyl acetal resin, diallyl phthalate resin, phenolic resin, epoxy resin, silicone resin, polysulfone resin and urea resin. These resins may be used singly (as a homopolymer) or in combination of two or more species (as a copolymer).

The anode (electrode) constituting the organic luminescence device of the present invention may desirably be formed of a material having a work function as large as possible. Examples of such a material may include: metals such as gold, platinum, nickel, palladium, cobalt, selenium and vanadium; alloys of those metals; and metal oxides such as tin oxide, zinc oxide, indium tin oxide (ITO) and indium zinc oxide. Further, it is also possible to use electroconductive polymers such as polyaniline, polypyrrole, polythiophene, and polyphenylene sulfide. These materials may be used singly or in mixture.

On the other hand, the cathode (electrode) may desirably be formed of a material having a work function as small as possible. Examples of such a material may include: metals such as lithium, sodium, potassium, calcium, magnesium, aluminum, indium, silver, lead, tin and chromium; and alloys of these metals. It is also possible to use metal oxides such as ITO. The cathode may be formed in a single layer or plural layers.

The substrate for the organic luminescence device of the present invention is not particularly limited. Examples of the substrate may include an opaque substrate such as a metal substrate or ceramic substrate, and a transparent substrate such as glass substrate, quartz substrate or plastic sheet. Further, it is also possible to control emission light by using a color filter film, a fluorescent color conversion film or a dielectric reflection film, in combination with the substrate.

The organic luminescence device of the present invention may further comprise a protective layer or a sealing layer in order to prevent contact of the organic luminescence device with ambient oxygen or moisture.

Examples of the protective film may include: a diamond film, a film of inorganic material such as metal oxide or metal nitride, a film of polymer such as fluorine-containing resin, polyparaxylene, polyethylene, silicone resin or polystyrene, and a photo-curable resin. Further, it is possible to effect packaging of the organic luminescence device per se by covering, e.g., glass substrate, gas-impermeable film or metal film with an appropriate sealing resin.

Incidentally, it is possible to cause white luminescence by incorporating a yellow luminescence material into the organic luminescence device of the present invention. For example, when rubrene as the yellow luminescence material is contained in a hole transport layer, white luminescence can be realized as specifically substantiated in Example 64 appearing hereinafter.

Hereinbelow, the present invention will be described more specifically based on Examples but is not restricted to the Examples.

SYNTHESIS EXAMPLE 1

Synthesis of Ex. Comp. No. 22

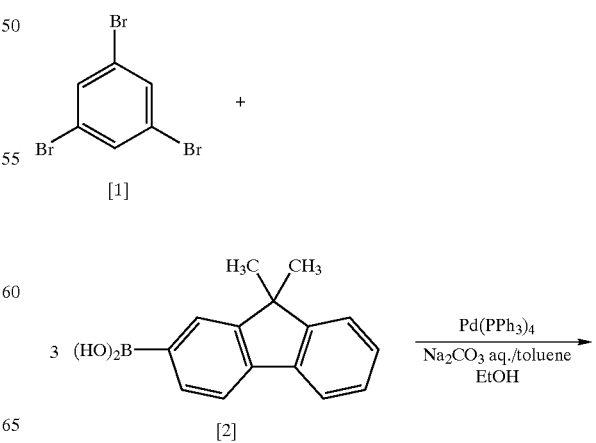

In a 500 ml-three necked flask, 0.8 g (2.52 mM) of 1,3,5-tribromobenzene[1], 3.0 g (12.6 mM) of fluorene-based boric acid [2], 160 ml of toluene and 80 ml of ethanol were placed and stirred in a nitrogen atmosphere at room temperature.

To the mixture, an aqueous solution of 15 g of sodium carbonate in 75 g of water was added dropwise and then 0.44 g (0.378 mM) of tetrakis (triphenylphosphine)palladium (0) was added. The system was stirred for 30 minutes at room temperature and heated up to 77° C., followed by stirring for 3 hours.

After the reaction, the reaction mixture was subjected to extraction of the organic layer with chloroform and dried with anhydrous sodium sulfate, followed by purification by silica gel column chromatography (eluent: hexane/toluene) to obtain 1.27 g of an objective compound (Ex. Comp. No. 22) (white crystal: Yield: 77%).

SYNTHESIS EXAMPLE 2

Synthesis of Ex. Comp. No. 64

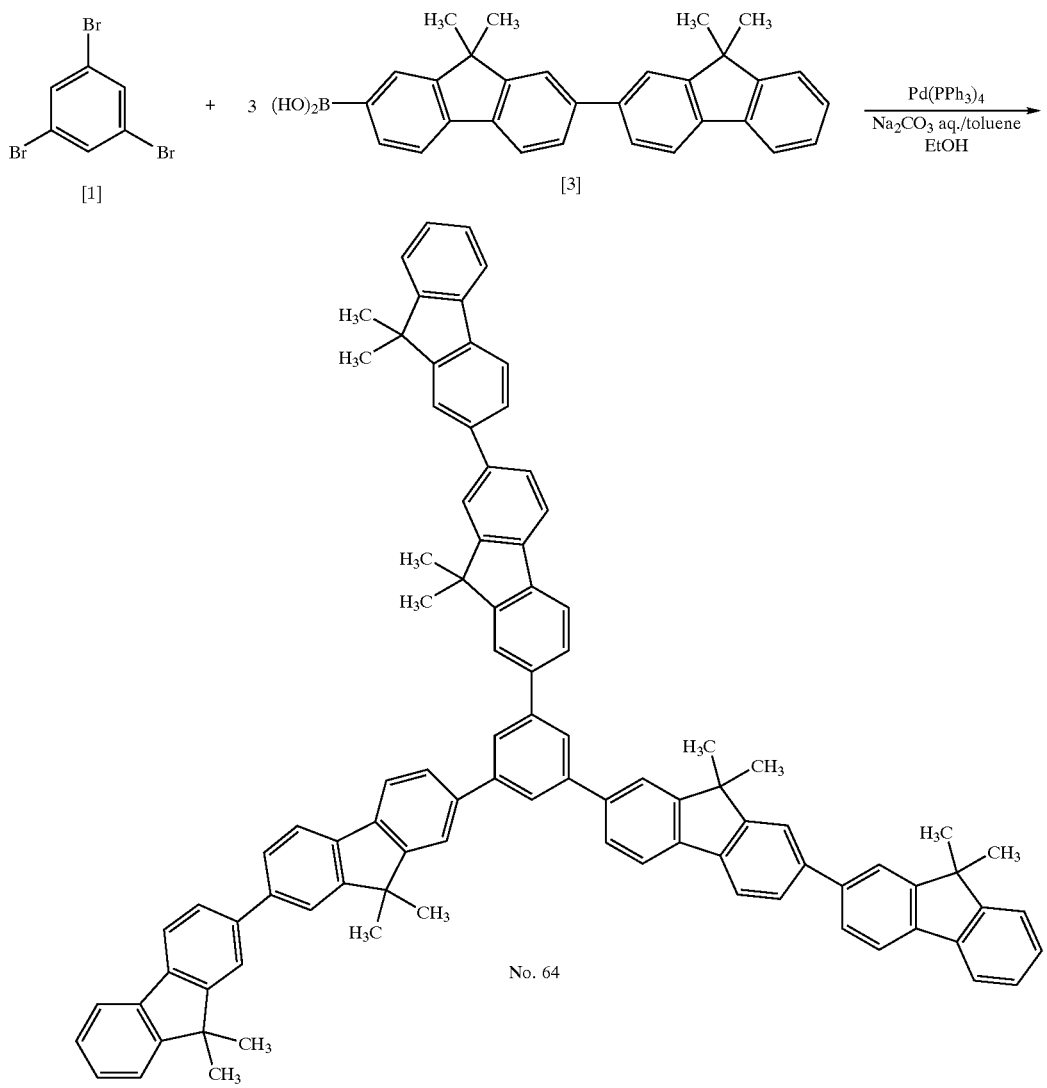

In a 500 ml-three necked flask, 0.8 g (2.52 mM) of 1,3,5-tribromobenzene[1], 4.8 g (12.6 mM) of fluorene-based boric acid [3], 160 ml of toluene and 80 ml of ethanol were placed and stirred in a nitrogen atmosphere at room temperature.

To the mixture, an aqueous solution of 15 g of sodium carbonate in 75 g of water was added dropwise and then 0.44 g (0.378 mM) of tetrakis (triphenylphosphine)palladium (0) was added. The system was stirred for 30 minutes at room temperature and heated up to 77° C., followed by stirring for 3 hours.

After the reaction, the reaction mixture was subjected to extraction of the organic layer with chloroform and dried with anhydrous sodium sulfate, followed by purification by silica gel column chromatography (eluent: hexane/toluene) to obtain 2.00 g of an objective compound (Ex. Comp. No. 64) (white crystal: Yield:. 73%).

SYNTHESIS EXAMPLE 3

Synthesis of Ex. Comp. No. 65

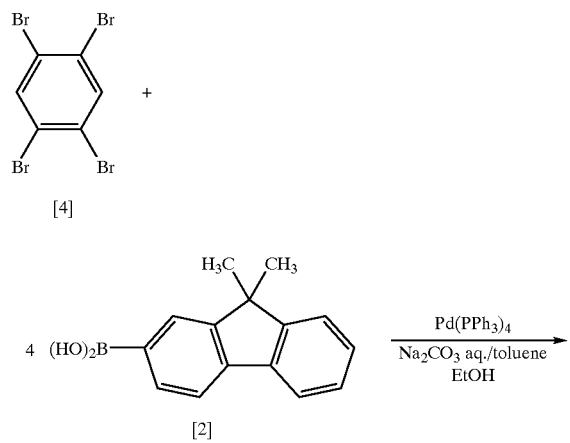

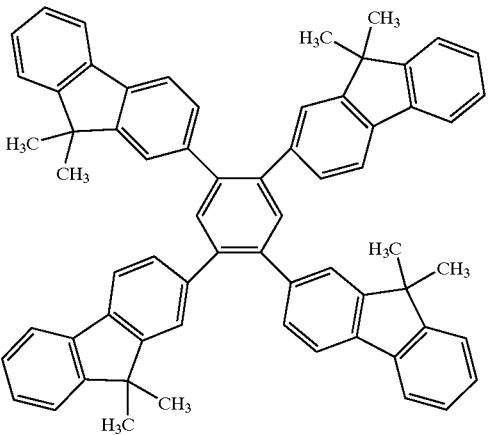

No. 65

In a 500 ml-three necked flask, 0.75 g (1.88 mM) of 1,2,4,5-tetrabromobenzene [4], 3.0 g (12.6 mM) of fluorene-based boric acid [2], 160 ml of toluene and 80 ml of ethanol were placed and stirred in a nitrogen atmosphere at room temperature.

To the mixture, an aqueous solution of 15 g of sodium carbonate in 75 g of water was added dropwise and then 0.43 g (0.376 mM) of tetrakis (triphenylphosphine)palladium (0) was added. The system was stirred for 30 minutes at room temperature and heated up to 77° C., followed by stirring for 5 hours.

After the reaction, the reaction mixture was subjected to extraction of the organic layer with chloroform and dried with anhydrous sodium sulfate, followed by purification by silica gel column chromatography (eluent: hexane/toluene) to obtain 1.41 g of an objective compound (Ex. Comp. No. 65) (white crystal: Yield: 88%).

SYNTHESIS EXAMPLE 4

Synthesis of Ex. Comp. No. 66

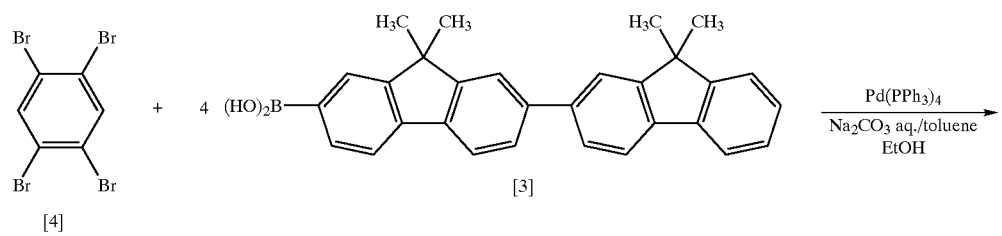

-continued

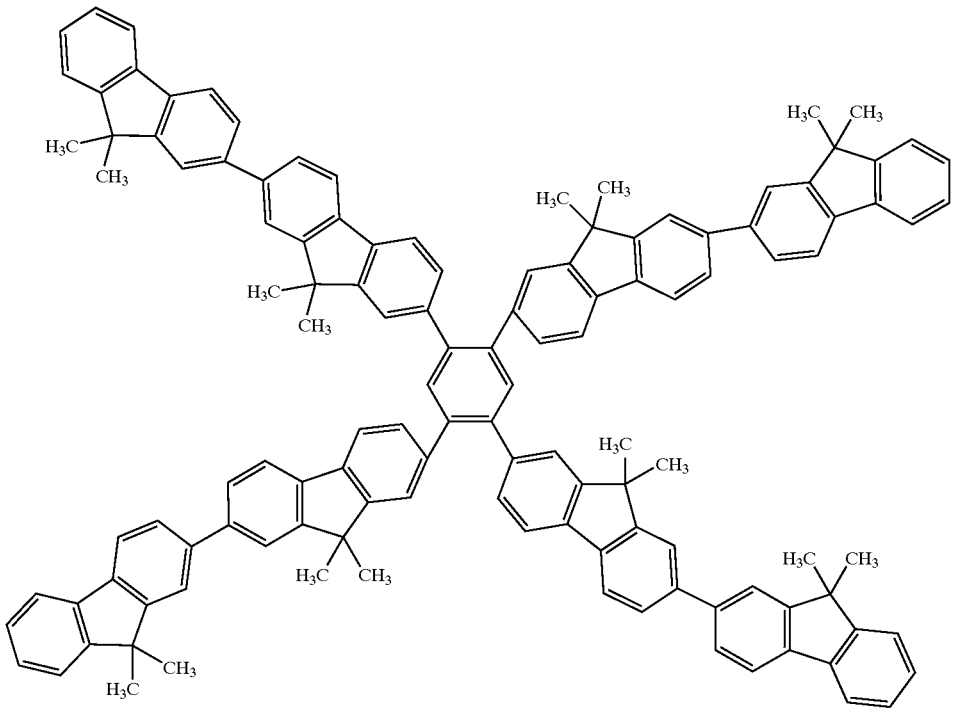

No. 66

In a 500 ml-three necked flask, 0.75 g (2.52 mM) of 1,2,4,5-tetrabromobenzene [4], 4.8 g (12.6 mM) of fluorene-based boric acid [3], 160 ml of toluene and 80 ml of ethanol were placed and stirred in a nitrogen atmosphere at room temperature.

To the mixture, an aqueous solution of 15 g of sodium carbonate in 75 g of water was added dropwise and then 0.43 g (0.376 mM) of tetrakis (triphenylphosphine)palladium (0) was added. The system was stirred for 30 minutes at room temperature and heated up to 77° C., followed by stirring for 5 hours.

After the reaction, the reaction mixture was subjected to extraction of the organic layer with chloroform and dried with anhydrous sodium sulfate, followed by purification by silica gel column chromatography (eluent: hexane/toluene) to obtain 1.88 g of an objective compound (Ax. Comp. No. 66) (white crystal: Yield: 70%).

EXAMPLE 1

An organic luminescence device shown in FIG. 2 was prepared in the following manner.

On a 0.7 mm-thick glass substrate 1, a 120 nm-thick ITO (indium tin oxide) film (anode 2) was formed by sputtering to prepare a transparent electroconductive support, which was then successively subjected to ultrasonic cleaning with acetone and with isopropyl alcohol (IPA). The resultant transparent electroconductive support was then subjected to boiling leaning with IPA and was dried, followed by UV/ozone cleaning.

On the transparent electroconductive support, a solution of a hole transport material shown below in chloroform was applied by spin coating to form a 30 nm-thick hole transport layer 5.

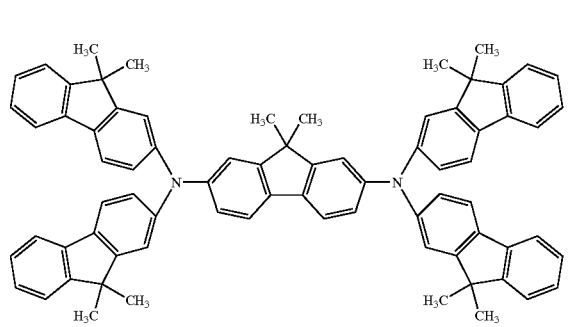

On the hole transport layer 5, a 50 nm-thick electron transport layer 6 of a fused polynuclear compound (Ex. Comp. No. 1) was formed by vacuum deposition under conditions including a vacuum degree (pressure) of $1.0 \times 10^{-4}$ Pa and a deposition rate of 0.2–0.3 nm/sec.

Then, on the electron transport layer 6, a 150 nm-thick metal electrode (cathode 4) of an aluminum-lithium alloy (Li content: 1 atomic %) was formed by vacuum deposition ($1.0 \times 10^{-4}$ Pa/1.0–1.2 nm/sec).

To the thus-prepared organic luminescence device, a DC voltage of 10 volts was applied between the ITO electrode (anode 2, positive pole) and the Al—Li electrode (cathode 4, negative pole), whereby a current was passed through the organic luminescence device at a current density of 9.0 mA/cm² and blue luminescence was observed at a luminance of 750 cd/m².

Then, when the organic luminescence device was supplied with a voltage for 100 hours while keeping a current density of 7.0 mA/cm² in a nitrogen atmosphere, a luminance of 550 cd/m² (as initial luminance) was merely decreased to 470 cd/m² even after 100 hours of the voltage application, thus exhibiting a good durability. The results are also shown in Table 1 appearing hereinafter.

EXAMPLES 2–15

Organic luminescence devices were prepared and evaluated in the same manner as in Example 1 except that the fused polynuclear compound (Ex. Corp. No. 1) was changed to those (Ex. Comp. Nos. 5, 10, 16, 19, 24, 25, 31, 36, 39, 43, 46, 51, 58 and 63), respectively.

The results are shown in Table 1.

COMPARATIVE EXAMPLES 1–8

Organic luminescence devices were prepared and evaluated in the same manner as in Example 1 except that the fused polynuclear compound (Ex. Comp. No. 1) was changed to the following comparative compounds Nos. 1–8, respectively.

The results are shown in Table 2.

Comparative compound No. 1

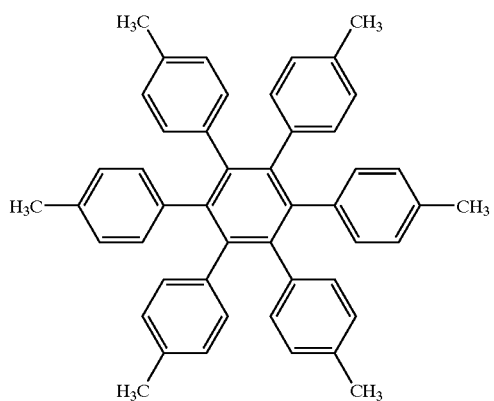

Comparative compound No. 2

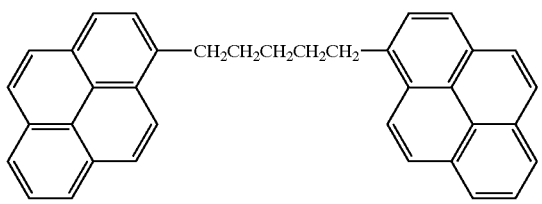

Comparative compound No. 3

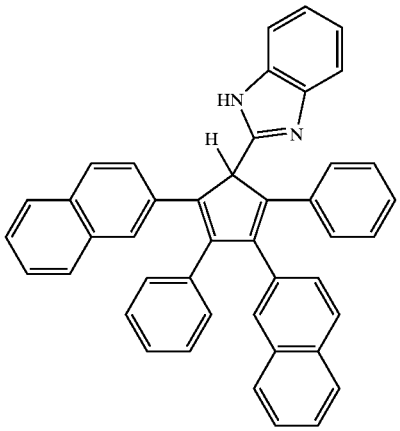

Comparative compound No. 4

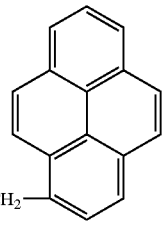

Comparative compound No. 5

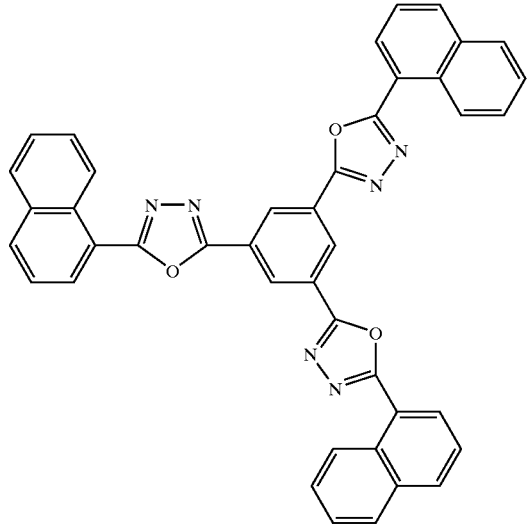

-continued

Comparative compound No. 6

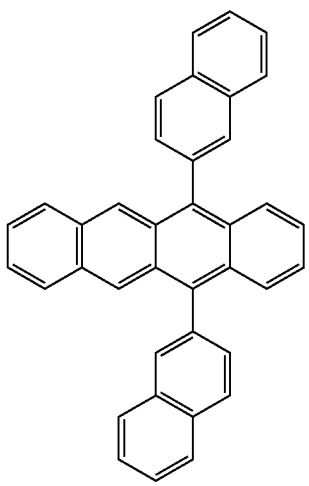

Comparative compound No. 7

Comparative compound No. 8

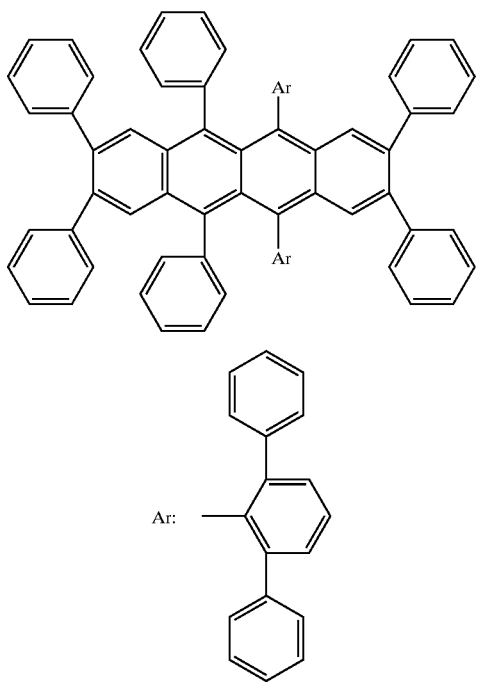

TABLE 1

| Ex. No. | Comp. No. | Applied voltage (V) | Initial Luminance (cd/m$^2$) | Luminance (at 7.0 mA/cm$^2$) Initial (cd/m$^2$) | After 100 hr (cd/m$^2$) |
|---|---|---|---|---|---|
| 1 | 1 | 10 | 750 | 550 | 470 |
| 2 | 5 | 10 | 640 | 480 | 440 |
| 3 | 10 | 10 | 670 | 510 | 470 |
| 4 | 16 | 10 | 1220 | 1130 | 810 |
| 5 | 19 | 10 | 880 | 690 | 610 |
| 6 | 24 | 10 | 560 | 530 | 430 |
| 7 | 25 | 10 | 920 | 780 | 650 |
| 8 | 31 | 10 | 960 | 830 | 740 |
| 9 | 36 | 10 | 580 | 490 | 430 |
| 10 | 39 | 10 | 660 | 520 | 460 |
| 11 | 43 | 10 | 570 | 510 | 440 |
| 12 | 46 | 10 | 720 | 570 | 510 |
| 13 | 51 | 10 | 710 | 550 | 490 |
| 14 | 58 | 10 | 1100 | 980 | 800 |
| 15 | 63 | 10 | 650 | 520 | 450 |

TABLE 2

| Comp. Ex. No. | Comp. No. | Applied voltage (V) | Initial Luminance (cd/m$^2$) | Luminance (at 7.0 mA/cm$^2$) Initial (cd/m$^2$) | After 100 hr (cd/m$^2$) |
|---|---|---|---|---|---|
| 1 | Comp. 1 | 10 | 140 | 100 | 10 |
| 2 | Comp. 2 | 10 | 70 | 60 | No luminescence |
| 3 | Comp. 3 | 10 | 90 | 70 | No luminescence |
| 4 | Comp. 4 | 10 | 80 | 70 | No luminescence |
| 5 | Comp. 5 | 10 | 150 | 90 | No luminescence |
| 6 | Comp. 6 | 10 | 290 | 200 | 40 |
| 7 | Comp. 7 | 10 | 190 | 160 | 20 |
| 8 | Comp. 8 | 10 | 320 | 240 | 80 |

EXAMPLE 16

An organic luminescence device shown in FIG. 3 was prepared in the following manner.

In a similar-manner as in Example 1, on a transparent electroconductive support, a 120 nm-thick ITO film (anode 2) and a 30 nm-thick hole transport layer 5 were formed.

On the hole transport layer 5, a 20 nm-thick luminescence layer 3 of a fused polynuclear compound (Ex. Comp. No. 4) was formed by vacuum deposition (1.0×10$^4$ Pa; 0.2–0.3 nm/sec).

On the luminescence layer 3, a 40 nm-thick electron transport layer 6 of tris-(8-hydroxy-quinoline)aluminum (Alq3) was formed by vacuum deposition (1.0×10$^{-4}$ Pa; 0.2–0.3 nm/sec).

Then, on the electron transport layer 6, a 150 nm-thick metal electrode (cathode 4) of an aluminum-lithium alloy (Li content: 1 atomic %) was formed by vacuum deposition (1.0×10$^{-4}$ Pa; 1.0–1.2 nm/sec).

To the thus-prepared organic luminescence device, a DC voltage of 8 volts was applied between the ITO electrode (anode 2, positive pole) and the Al—Li electrode (cathode 4, negative pole), whereby a current was passed through the organic luminescence device at a current density of 8.1 mA/cm² and blue luminescence was observed at a luminance of 3980 cd/m².

Then, when the organic luminescence device was supplied with a voltage for 100 hours while keeping a current density of 7.0 mA/cm² in a nitrogen atmosphere, a luminance of 3090 cd/m² (as initial luminance) was merely decreased to 2600 cd/m² even after 100 hours of the voltage application, thus exhibiting a good durability. The results are also shown in Table 3 appearing hereinafter.

EXAMPLES 17–30

Organic luminescence devices were prepared and evaluated in the same manner as in Example 16 except that the fused polynuclear compound (Ex. Comp. No. 4) was changed to those (Ex. Comp. Nos. 6, 11, 14, 18, 22, 27, 29, 35, 40, 42, 47, 49, 52 and 62), respectively.

The results are shown in Table 3.

COMPARATIVE EXAMPLES 9–16

Organic luminescence devices were prepared and evaluated in the same manner as in Example 16 except that the fused polynuclear compound (Ex. Comp. No. 4) was changed to the above-mentioned comparative compounds Nos. 1–8, respectively.

The results are shown in Table 4.

TABLE 3

| | | Initial | | |
|---|---|---|---|---|
| Ex. | | Applied | Luminance (at 7.0 mA/cm²) | |
| Ex. No. | Comp. No. | voltage (V) | Luminance (cd/m²) | Initial (cd/m²) | After 100 hr (cd/m²) |
| 16 | 4 | 8 | 3980 | 3090 | 2600 |
| 17 | 6 | 8 | 4140 | 3470 | 2480 |
| 18 | 11 | 8 | 7370 | 6510 | 4860 |
| 19 | 14 | 8 | 5320 | 4130 | 2990 |
| 20 | 18 | 8 | 7050 | 6600 | 5210 |
| 21 | 22 | 8 | 5560 | 4430 | 3310 |
| 22 | 27 | 8 | 5920 | 4790 | 3600 |
| 23 | 29 | 8 | 7760 | 7000 | 4940 |
| 24 | 35 | 8 | 3170 | 2770 | 2030 |
| 25 | 40 | 8 | 5160 | 4410 | 3200 |
| 26 | 42 | 8 | 6010 | 5300 | 4290 |
| 27 | 47 | 8 | 6990 | 6570 | 5100 |
| 28 | 49 | 8 | 7500 | 6380 | 5290 |
| 29 | 52 | 8 | 5300 | 4680 | 3800 |
| 30 | 62 | 8 | 4950 | 4000 | 3350 |

TABLE 4

| | | Initial | | |
|---|---|---|---|---|
| Comp. Ex. | | Applied | Luminance (at 7.0 mA/cm²) | |
| Comp. Ex. No. | Comp. No. | voltage (V) | Luminance (cd/m²) | Initial (cd/m²) | After 100 hr (cd/m²) |
| 9 | Comp. 1 | 8 | 640 | 450 | 60 |
| 10 | Comp. 2 | 8 | 470 | 430 | No luminescence |
| 11 | Comp. 3 | 8 | 340 | 270 | No luminescence |
| 12 | Comp. 4 | 8 | 490 | 420 | No luminescence |
| 13 | Comp. 5 | 8 | 650 | 490 | No luminescence |
| 14 | Comp. 6 | 8 | 1700 | 1000 | 140 |
| 15 | Comp. 7 | 9 | 1180 | 860 | 90 |
| 16 | Comp. 8 | 8 | 2120 | 1240 | 360 |

EXAMPLE 31

An organic luminescence device shown in FIG. 3 was prepared in the following manner.

On a transparent electroconductive support prepared in the same manner as in Example 1, a solution of a hole transport material shown below in chloroform was applied by spin coating to form a 20 nm-thick hole transport layer 5.

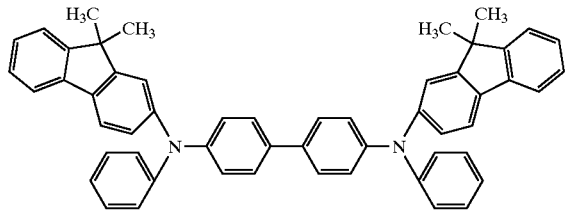

On the hole transport layer 5, a 20 nm-thick co-deposited luminescence layer 3 of compound shown below fused polynuclear compound (Ex. Comp. No. 2) (1/50 by weight) was formed by vacuum deposition (1.0×10⁴ Pa; 0.2–0.3 nm/sec).

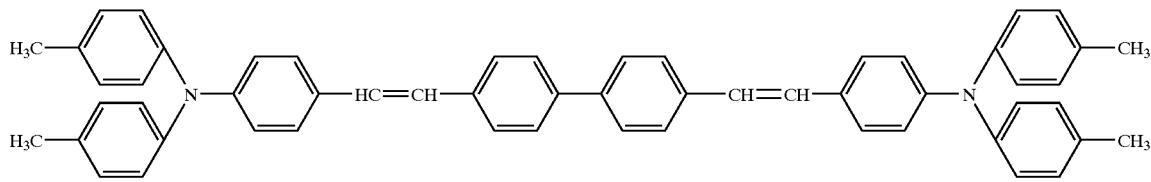

On the luminescence layer 3, a 40 nm-thick electron transport layer 6 of tris-18-hydroxy-quinoline)aluminum (Alq3) was formed by vacuum deposition ($1.0\times10^{-4}$ Pa; 0.2–0.3 nm/sec).

Then, on the electron transport layer 6, a 150 nm-thick metal electrode (cathode 4) of an aluminum-lithium alloy (Li content: 1 atomic %) was formed by vacuum deposition ($1.0\times10^{-4}$ Pa; 1.0–1.2 nm/sec).

To the thus-prepared organic luminescence device, a DC voltage of 8 volts was applied between the ITO electrode (anode 2, positive pole) and the Al—Li electrode (cathode 4, negative pole), whereby a current was passed through the organic luminescence device at a current density of 8.5 mA/cm$^2$ and bluish white luminescence was observed at a luminance of 46500 cd/m$^2$.

Then, when the organic luminescence device was supplied with a voltage for 100 hours while keeping a current density of 5.0 mA/cm$^2$ in a nitrogen atmosphere; a luminance of 22500 cd/m$^2$ (as initial luminance) was merely decreased to 17600 cd/m$^2$ even after 100 hours of the voltage application, thus exhibiting a good durability. The results are also shown in Table 5 appearing hereinafter.

EXAMPLES 32–45

Organic luminescence devices were prepared and evaluated in the same manner as in Example 31 except that the fused polynuclear compound (Ex. Comp. No. 2) was changed to those (Ex. Comp. Nos. 7, 9, 15, 17, 23, 28, 32, 34, 38, 41, 45, 50, 53 and 56), respectively.

The results are shown in Table 5.

COMPARATIVE EXAMPLES 17–24

Organic luminescence devices were prepared and evaluated in the same manner as in Example 31 except that the fused polynuclear compound (Ex. Comp. No. 2) was changed to the above-mentioned comparative compounds Nos. 1–8, respectively.

The results are shown in Table 6.

TABLE 5

| Ex. No. | Ex. Comp. No. | Applied voltage (V) | Luminance (cd/m$^2$) | Initial (cd/m$^2$) | After 100 hr (cd/m$^2$) |
|---|---|---|---|---|---|
| | | | | Initial | Luminance (at 5.0 mA/cm$^2$) |
| 31 | 2  | 8 | 46500 | 22500 | 17600 |
| 32 | 7  | 8 | 24300 | 13500 | 10900 |
| 33 | 9  | 8 | 78300 | 39000 | 32100 |
| 34 | 15 | 8 | 66000 | 35400 | 29800 |
| 35 | 17 | 8 | 69600 | 37000 | 33300 |
| 36 | 23 | 8 | 45600 | 23000 | 18500 |
| 37 | 28 | 8 | 55200 | 29000 | 25600 |
| 38 | 32 | 8 | 67700 | 37000 | 30800 |
| 39 | 34 | 8 | 43200 | 24000 | 16500 |
| 40 | 38 | 8 | 41000 | 20000 | 15500 |
| 41 | 41 | 8 | 46700 | 25300 | 20900 |
| 42 | 45 | 8 | 59800 | 34100 | 25000 |
| 43 | 50 | 8 | 39700 | 26400 | 22000 |
| 44 | 53 | 8 | 62300 | 34000 | 28700 |
| 45 | 56 | 8 | 44300 | 26800 | 20800 |

TABLE 6

| Comp. Ex. No. | Comp. Comp. No. | Applied voltage (V) | Luminance (cd/m$^2$) | Initial (cd/m$^2$) | After 100 hr (cd/m$^2$) |
|---|---|---|---|---|---|
| | | | | Initial | Luminance (at 5.0 mA/cm$^2$) |
| 17 | Comp. 1 | 8 | 1190 | 650  | 130 |
| 18 | Comp. 2 | 8 | 770  | 460  | No luminescence |
| 19 | Comp. 3 | 8 | 650  | 390  | No luminescence |
| 20 | Comp. 4 | 8 | 690  | 390  | No luminescence |
| 21 | Comp. 5 | 8 | 1250 | 880  | 140 |
| 22 | Comp. 6 | 8 | 5700 | 2610 | 870 |
| 23 | Comp. 7 | 8 | 3180 | 1820 | 760 |
| 24 | Comp. 8 | 8 | 7220 | 3540 | 1360 |

EXAMPLE 46

An organic luminescence device shown in FIG. 5 was prepared in the following manner.

On a transparent electroconductive support prepared in the same manner as in Example 1, a 20 nm-thick hole transport layer 5 was formed in the same manner as in Example 31.

On the hole transport layer 5, a 20 nm-thick co-deposited luminescence layer 3 of rubrene/Alq3 (1:20 by weight) was formed by vacuum deposition ($1.0\times10^{-4}$ Pa 0.2–0.3 nm/sec).

On the luminescence layer 3, a 10 nm-thick hole/exciton blocking layer 8 of a fused polynuclear compound (Ex. Comp. No. 3) was formed by vacuum deposition ($1.0\times10^{-4}$ Pa; 0.2–0.3 nm/sec).

On the blocking layer 8, a 40 nm-thick electron transport layer 6 of Alq3 was formed by vacuum deposition ($1.0\times10^{-4}$ Pa; 0.2–0.3 nm/sec).

Then, on the electron transport layer 6, a 150 nm-thick metal electrode (cathode 4) of an aluminum-lithium alloy (Li content: 1 atomic %) was formed by vacuum deposition ($1.0\times10^{-4}$ Pa; 1.0–1.2 nm/sec).

To the thus-prepared organic luminescence device, a DC voltage of 10 volts was applied between the ITO electrode (anode 2, positive pole) and the Al—Li electrode (cathode 4, negative pole), whereby a current was passed through the organic luminescence device at a current density of 8.9 mA/cm$^2$ and yellowish green luminescence was observed at a luminance of 60200 cd/m$^2$.

Then, when the organic luminescence device was supplied with a voltage for 100 hours while keeping a current density of 7.0 mA/cm$^2$ in a nitrogen atmosphere, a luminance of 38000 cd/m$^2$ (as initial luminance) was merely decreased to 28700 cd/m$^2$ even after 100 hours of the voltage application, thus exhibiting a good durability. The results are also shown in Table 7 appearing hereinafter.

EXAMPLES 47–60

Organic luminescence devices were prepared and evaluated in the same manner as in Example 46 except that the fused polynuclear compound (Ex. Comp. No. 3) was changed to those (Ex. Comp. Nos. 8, 13, 21, 30, 33, 37, 44, 48, 54, 55, 57, 59, 60 and 61), respectively.

The results are shown in Table 7.

COMPARATIVE EXAMPLES 25–32

Organic luminescence devices were prepared and evaluated in the same manner as in Example 46 except that the fused polynuclear compound (Ex. Comp. No. 3) was changed to the above-mentioned comparative compounds Nos. 1–8, respectively.

The results are shown in Table 8.

TABLE 7

| Ex. No. | Ex. Comp. No. | Applied voltage (V) | Initial Luminance (cd/m²) | Luminance (at 7.0 mA/cm²) Initial (cd/m²) | After 100 hr (cd/m²) |
|---|---|---|---|---|---|
| 46 | 3 | 10 | 60200 | 38000 | 28700 |
| 47 | 8 | 10 | 41000 | 24500 | 15500 |
| 48 | 13 | 10 | 62400 | 39300 | 30100 |
| 49 | 21 | 10 | 61100 | 38500 | 29900 |
| 50 | 30 | 10 | 79700 | 47000 | 34100 |
| 51 | 33 | 10 | 77600 | 45800 | 31200 |
| 52 | 37 | 10 | 42500 | 26000 | 15800 |
| 53 | 44 | 10 | 67700 | 37000 | 30800 |
| 54 | 48 | 10 | 80200 | 47000 | 34400 |
| 55 | 54 | 10 | 42900 | 24200 | 16500 |
| 56 | 55 | 10 | 76600 | 45300 | 31800 |
| 57 | 57 | 10 | 49900 | 27300 | 15000 |
| 58 | 59 | 10 | 39200 | 24400 | 15700 |
| 59 | 60 | 10 | 42500 | 28000 | 18700 |
| 60 | 61 | 10 | 42300 | 26300 | 17000 |

TABLE 8

| Comp. Ex. No. | Comp. No. | Applied voltage (V) | Initial Luminance (cd/m²) | Luminance (at 7.0 mA/cm²) Initial (cd/m²) | After 100 hr (cd/m²) |
|---|---|---|---|---|---|
| 25 | Comp. 1 | 10 | 1020 | 660 | 120 |
| 26 | Comp. 2 | 10 | 750 | 420 | No luminescence |
| 27 | Comp. 3 | 10 | 680 | 410 | No luminescence |
| 28 | Comp. 4 | 10 | 690 | 420 | No luminescence |
| 29 | Comp. 5 | 10 | 1050 | 750 | 210 |
| 30 | Comp. 6 | 10 | 5400 | 2200 | 770 |
| 31 | Comp. 7 | 10 | 2850 | 1600 | 560 |
| 32 | Comp. 8 | 10 | 8010 | 3670 | 910 |

EXAMPLE 61

An organic luminescence device shown in FIG. 1 was prepared in the following manner.

On a transparent electroconductive support prepared in the same manner as in Example 1, a solution of a mixture comprising 0.050 g of a fused polynuclear compound (Ex. Comp. No. 12) and 1.00 g of poly-N-vinylcarbazole (weight-average molecular weight=63,000) in 80 ml of chloroform was applied by spin coating (2000 rpm) to form a 120 nm-thick luminescence layer 3.

Then, on the luminescence layer 3, a 150 nm-thick metal electrode (cathode 4) of an aluminum-lithium alloy (Li content: 1 atomic %) was formed by vacuum deposition ($1.0 \times 10^{-4}$ Pa; 1.0–1.2 nm/sec).

To the thus-prepared organic luminescence device, a DC voltage of 10 volts was applied between the ITO electrode (anode 2, positive pole) and the Al—Li electrode (cathode 4, negative pole), whereby a current was passed through the organic luminescence device at a current density of 7.8 mA/cm² and blue luminescence was observed at a luminance of 1250 cd/m².

Then, when the organic luminescence device was supplied with a voltage for 100 hours while keeping a current density of 5.0 mA/cm² in a nitrogen atmosphere, a luminance of 820 cd/m² (as initial luminance) was merely decreased to 670 cd/m² even after 100 hours of the voltage application, thus exhibiting a good durability. The results are also shown in Table 9 appearing hereinafter.

EXAMPLES 62 and 63

Organic luminescence devices were prepared and evaluated in the same manner as in Example 61 except that the fused polynuclear compound (Ex. Comp. No. 12) was changed to those (Ex. Comp. Nos. 20 and 26), respectively.

The results are shown in Table 9.

COMPARATIVE EXAMPLES 33–40

Organic luminescence devices were prepared and evaluated in the same manner as in Example 61 except that the fused polynuclear compound (Ex. Comp. No. 12) was changed to the above-mentioned comparative compounds Nos. 1–8, respectively.

The results are shown in Table 9.

TABLE 9

| Ex. or Comp. Ex. | Ex. Comp. No. | Applied voltage (V) | Initial Luminance (cd/m²) | Luminance (at 5.0 mA/cm²) Initial (cd/m²) | After 100 hr (cd/m²) |
|---|---|---|---|---|---|
| Ex. 61 | 12 | 10 | 1250 | 820 | 670 |
| Ex. 62 | 20 | 10 | 980 | 670 | 590 |
| Ex. 63 | 26 | 10 | 1070 | 740 | 610 |
| Comp. Ex. 33 | Comp. 1 | 10 | 230 | 150 | No luminescence |
| Comp. Ex. 34 | Comp. 2 | 10 | 120 | 80 | No luminescence |
| Comp. Ex. 35 | Comp. 3 | 10 | 90 | 70 | No luminescence |
| Comp. Ex. 36 | Comp. 4 | 10 | 80 | 60 | No luminescence |
| Comp. Ex. 37 | Comp. 5 | 10 | 250 | 150 | No luminescence |
| Comp. Ex. 38 | Comp. 6 | 10 | 340 | 220 | 40 |
| Comp. Ex. 39 | Comp. 7 | 10 | 340 | 210 | 20 |
| Comp. Ex. 40 | Comp. 8 | 10 | 410 | 270 | 80 |

EXAMPLE 64

An organic luminescence device shown in FIG. 3 was prepared in the following manner.

On a transparent electroconductive support prepared in the same manner as in Example 1, a mixture of hole transport material shown below with rubrene (yellow luminescence material) (100/1 by weight) was formed by vacuum deposition ($1.0 \times 10^{-4}$ Pa; 0.2–0.3 nm/sec) to form a 50 nm-thick hole transport layer 5.

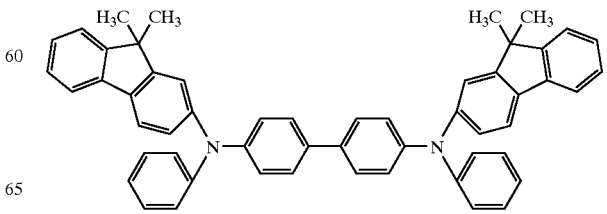

On the hole transport layer 5, a 20 nm-thick luminescence layer 3 of a mixture of a compound shown below with a fused polynuclear compound (Ex. Comp. No. 9) (1/100 by weight) was formed by vacuum deposition (1.0×10⁴ Pa; 0.2–0.3 nm/sec).

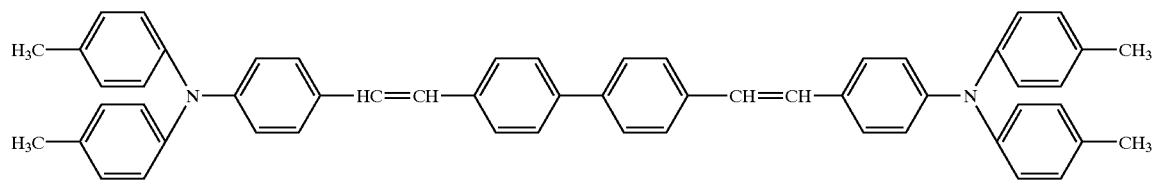

On the luminescence layer 3, a 30 nm-thick electron transport layer 6 of Alq3 was formed by vacuum deposition (1.0×10⁻⁴ Pa; 0.2–0.3 nm/sec).

Then, on the electron transport layer 6, a 150 nm-thick metal electrode (cathode 4) of an aluminum-lithium alloy (Li content: 1 atomic %) was formed by vacuum deposition (1.0×10⁻⁴ Pa; 1.0–1.2 nm/sec).

To the thus-prepared organic luminescence device, a DC voltage of 8 volts was applied between the ITO electrode (anode 2, positive pole) and the Al—Li electrode (cathode 4, negative pole), whereby a current was passed through the organic luminescence device at a current density of 100 mA/cm² and white luminescence was observed at a luminance of 11000 cd/m².

Then, when the organic luminescence device was supplied with a DC voltage of 15 volts, a current was passed through the organic luminescence device at a current density of 2250 mA/cm² and white luminescence was observed at a luminance of 213000 cd/m².

EXAMPLES 65–67

Organic luminescence devices were prepared and evaluated in the same manner as in Example 1 except that the fused polynuclear compound (Ex. Comp. No. 1) was changed to those (Ex. Comp. Nos. 64, 65 and 66), respectively.

The results are shown in Table 10.

TABLE 10

| Ex. No. | Ex. Comp. No. | Initial Applied voltage (V) | Luminance (cd/m²) | Luminance (at 7.0 mA/cm²) Initial (cd/m²) | After 100 hr (cd/m²) |
|---|---|---|---|---|---|
| 65 | 64 | 10 | 1900 | 1500 | 1400 |
| 66 | 65 | 10 | 2400 | 1800 | 1600 |
| 67 | 66 | 10 | 1500 | 1400 | 1200 |

EXAMPLES 68–70

Organic luminescence devices were prepared and evaluated in the same manner as in Example 16 except that the fused polynuclear compound (Ex. Comp. No. 4) was changed to those (Ex. Comp. Nos. 64, 65 and 66), respectively.

The results are shown in Table 11.

TABLE 11

| Ex. No. | Ex. Comp. No. | Initial Applied voltage (V) | Luminance (cd/m²) | Luminance (at 7.0 mA/cm²) Initial (cd/m²) | After 100 hr (cd/m²) |
|---|---|---|---|---|---|
| 68 | 64 | 8 | 11000 | 9000 | 7000 |
| 69 | 65 | 8 | 14000 | 12500 | 9000 |
| 70 | 66 | 8 | 9500 | 8500 | 7000 |

EXAMPLES 71–74

The organic luminescence devices prepared in Examples 21, 68, 69 and 70 were subjected to measurement off CIE chromaticity coordinates (X, Y) by using an emission spectrometer ("Photal MCPD-7000", mfd. by Otsuka Electronics. Co. Ltd.).

The results are shown in Table 12.

TABLE 12

| Ex. No. | Ex. Comp. No. | CIE chromaticity coordinates (X, Y) |
|---|---|---|
| 71 | 22 | (0.14, 0.08) |
| 72 | 64 | (0.16, 0.12) |
| 73 | 65 | (0.15, 0.09) |
| 74 | 66 | (0.16, 0.13) |

From the above results, it has been found that the fused polynuclear compounds (Ex. Comp. Nos. 22, 64, 65 and 66) used in the present invention were effective to cause blue luminescence with excellent purity.

As described hereinabove, according to the present invention, by using a fused polynuclear compound of the formula (I) to (VII) as a material for organic luminescence function layer, particularly for an electron transport layer, a luminescence layer or a hole/exciton blocking layer, in an organic luminescence device, the resultant organic luminescence device allows a high-luminance luminescence at a lower applied voltage and is also excellent in durability.

The organic luminescence device of the present invention can be readily prepared by vacuum deposition or wet coating, thus being produced in a large-area device relatively inexpensively.

What is claimed is:

1. A device, comprising:
a pair of an anode and a cathode, and
at least one organic luminescence layer disposed between the anode and the cathode,
wherein said at least one organic luminescence layer comprises a layer of a compound represented by the following formula (VII):

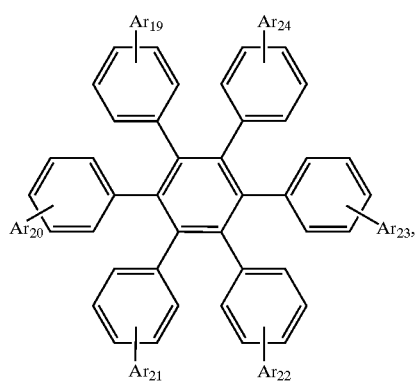

(VII)

wherein each one of $Ar_{19}$, $Ar_{20}$, $Ar_{21}$, $Ar_{22}$, $Ar_{23}$ and $Ar_{24}$ is the same substituted or unsubstituted fused polynuclear carbocylic aromatic group or substituted or unsubstituted acrydinyl or fluorenonyl group.

2. The device according to claim 1, wherein $Ar_{19}$, $Ar_{20}$, $Ar_{21}$, $Ar_{22}$, $Ar_{23}$ and $Ar_{24}$ are selected from the group consisting of formulas (VIII), (IX), (X) and (XIII):

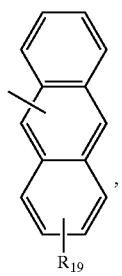

(VIII)

wherein $R_{19}$ is a hydrogen atom, an alkyl group, a substituted or unsubstituted aralkyl group, a substituted or unsubstituted aryl group, a substituted or unsubstituted heterocyclic group, a substituted amino group or a cyano group;

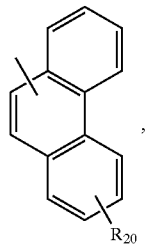

(IX)

wherein $R_{20}$ is a hydrogen atom, an alkyl group, a substituted or unsubstituted aralkyl group, a substituted or unsubstituted aryl group, a substituted or unsubstituted heterocyclic group, a substituted amino group or a cyano group;

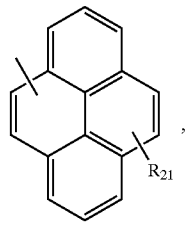

(X)

wherein $R_{21}$ is a hydrogen atom, an alkyl group, a substituted or unsubstituted aralkyl group, a substituted or unsubstituted aryl group, a substituted or unsubstituted heterocyclic group, a substituted amino group or a cyano group; or

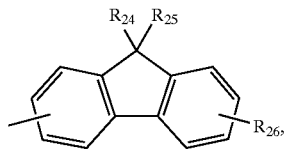

(XIII)

wherein $R_{24}$, $R_{25}$ and $R_{26}$ independently denote a hydrogen atom, an alkyl group, a substituted or unsubstituted aralkyl group, a substituted or unsubstituted aryl group, a substituted or unsubstituted heterocyclic group, a substituted amino group or a cyano group.

* * * * *

UNITED STATES PATENT AND TRADEMARK OFFICE
CERTIFICATE OF CORRECTION

PATENT NO. : 6,994,922 B2  Page 1 of 3
APPLICATION NO. : 10/940734
DATED : February 7, 2006
INVENTOR(S) : Koichi Suzuki et al.

It is certified that error appears in the above-identified patent and that said Letters Patent is hereby corrected as shown below:

ON COVER PAGE AT (57) ABSTRACT

Line 7, "denote hydrogen" should read --denote a hydrogen--.

COLUMN 1

Line 36, "5,151,629" should read --5,151,629;--.

COLUMN 3

Line 58, "br" should read --or--.

COLUMN 14

Figure 14, " 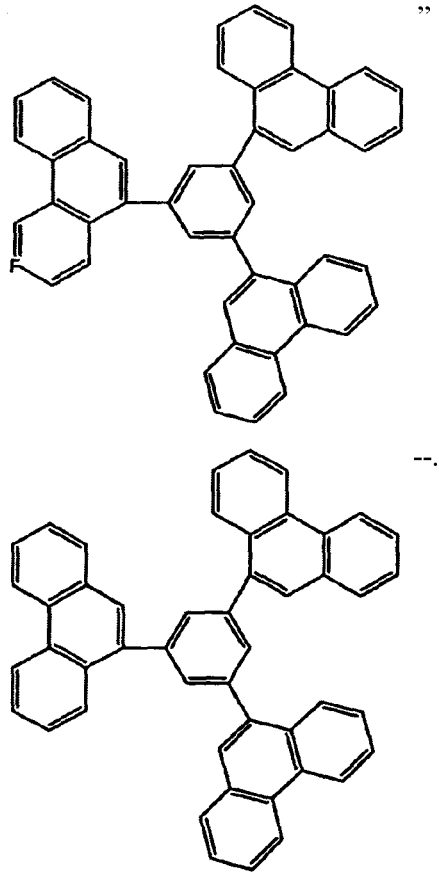 " should read -- --.

UNITED STATES PATENT AND TRADEMARK OFFICE
CERTIFICATE OF CORRECTION

| | | |
|---|---|---|
| PATENT NO. | : 6,994,922 B2 | |
| APPLICATION NO. | : 10/940734 | |
| DATED | : February 7, 2006 | |
| INVENTOR(S) | : Koichi Suzuki et al. | |

It is certified that error appears in the above-identified patent and that said Letters Patent is hereby corrected as shown below:

COLUMN 41

Line 60, "formed-in" should read --formed in--.

COLUMN 43

Line 5, "confining" should read --confine--; and
    Line 7, "luminescence-efficiency." should read --luminescence efficiency.--.

COLUMN 61

Line 65, "leaning" should read --cleaning--.

COLUMN 66

Line 47, "similar-manner" should read --similar manner--.

COLUMN 69

Line 2, "tris-18-hydroxy-quinoline)aluminum" should read --tris-(8-hydroxy-quinoline)aluminum--.

COLUMN 71

Line 2, "the:above-mentioned" should read --the above-mentioned--.

COLUMN 72

Line 13, "to-those" should read --to those--.

UNITED STATES PATENT AND TRADEMARK OFFICE
CERTIFICATE OF CORRECTION

PATENT NO. : 6,994,922 B2
APPLICATION NO. : 10/940734
DATED : February 7, 2006
INVENTOR(S) : Koichi Suzuki et al.

It is certified that error appears in the above-identified patent and that said Letters Patent is hereby corrected as shown below:

COLUMN 75

Line 29, "carbocylic" should read --carbocyclic--.

Signed and Sealed this

Fourteenth Day of November, 2006

JON W. DUDAS
*Director of the United States Patent and Trademark Office*